(12) United States Patent
Case et al.

(10) Patent No.: US 10,149,620 B2
(45) Date of Patent: Dec. 11, 2018

(54) METHODS AND SYSTEMS USING LED SOURCES TO CREATE CONTRAST AGENTS FOR MID-INFRARED IMAGING OF BLOOD VESSELS

(71) Applicants: Jason Case, Locust, NC (US); Susan Trammell, Charlotte, NC (US)

(72) Inventors: Jason Case, Locust, NC (US); Susan Trammell, Charlotte, NC (US)

(73) Assignee: The University Of North Carolina At Charlotte, Charlotte, NC (US)

( * ) Notice: Subject to any disclaimer, the term of this patent is extended or adjusted under 35 U.S.C. 154(b) by 0 days.

(21) Appl. No.: 15/031,361

(22) PCT Filed: Feb. 23, 2015

(86) PCT No.: PCT/US2015/017035
§ 371 (c)(1),
(2) Date: Apr. 22, 2016

(87) PCT Pub. No.: WO2016/018463
PCT Pub. Date: Feb. 4, 2016

(65) Prior Publication Data
US 2016/0287088 A1    Oct. 6, 2016

Related U.S. Application Data

(60) Provisional application No. 61/919,971, filed on Dec. 23, 2013.

(51) Int. Cl.
*A61B 5/026* (2006.01)
*A61B 5/01* (2006.01)
(Continued)

(52) U.S. Cl.
CPC .......... *A61B 5/015* (2013.01); *A61B 5/02007* (2013.01); *A61B 5/0261* (2013.01); *A61B 5/742* (2013.01)

(58) Field of Classification Search
CPC ..... A61B 5/015; A61B 5/742; A61B 5/02007; A61B 5/0261
(Continued)

(56) References Cited

U.S. PATENT DOCUMENTS 6,009,340 A * 12/1999 Hsia ................... A61B 5/00
                                                      348/164
6,023,637 A *  2/2000 Liu .................... A61B 5/015
                                                      128/922

(Continued)

FOREIGN PATENT DOCUMENTS

WO    2012009359 A2    1/2012

OTHER PUBLICATIONS

Jan. 8, 2016 International Search Report issued in International Patent Application No. PCT/US2015/017035.

*Primary Examiner* — Sanjay Cattungal
(74) *Attorney, Agent, or Firm* — Clements Bernard Walker PLLC; Christopher L. Bernard

(57) ABSTRACT

Novel methods and systems to map the structure of blood vessels and monitor the flow of blood through these vascular networks using thermal imaging techniques. To obtain high contrast thermal images of the vascular structure in tissue, there must be a temperature difference between the blood/blood vessels and surrounding tissue. If the blood and blood vessels are warmer than the surrounding tissue, the vessels will appear brighter in thermal infrared images. A temperature contrast between blood vessels and the surrounding tissue can be achieved through selective heating of the blood. Hemoglobin has major absorption peaks near 420 and 530 nm, while absorption due to water (the dominant component of soft tissue) is significantly lower at these (Continued)

wavelengths. Irradiation of blood and tissue at these wavelengths produces selective heating of the blood compared to the surrounding soft tissue.

17 Claims, 21 Drawing Sheets

(51) Int. Cl.
*A61B 5/02* (2006.01)
*A61B 5/00* (2006.01)

(58) Field of Classification Search
USPC .................................................. 600/473–480
See application file for complete search history.

(56) References Cited

U.S. PATENT DOCUMENTS

| | | | | |
|---|---|---|---|---|
| 9,622,662 B2* | 4/2017 | Zuzak | ................ | A61B 5/14551 |
| 9,719,937 B2* | 8/2017 | Kapelushnik | .......... | G01N 21/84 |
| 9,804,145 B2* | 10/2017 | Kapelushnik | ...... | G01N 21/3577 |
| 9,872,613 B2* | 1/2018 | Seibel | .................. | A61B 1/2733 |
| 2001/0055462 A1* | 12/2001 | Seibel | ................ | A61B 1/00048 |
| | | | | 385/147 |
| 2003/0044353 A1* | 3/2003 | Weissleder | ........... | C12Q 1/6816 |
| | | | | 424/9.6 |
| 2004/0236225 A1* | 11/2004 | Murphy | ................. | A61B 5/015 |
| | | | | 600/473 |
| 2006/0195014 A1* | 8/2006 | Seibel | .................. | A61B 1/0008 |
| | | | | 600/102 |
| 2007/0173727 A1* | 7/2007 | Naghavi | .................. | A61B 5/01 |
| | | | | 600/483 |
| 2007/0213617 A1* | 9/2007 | Berman | ............... | A61B 5/0091 |
| | | | | 600/473 |
| 2009/0048523 A1* | 2/2009 | Schlagheck | .......... | A61B 5/0073 |
| | | | | 600/473 |
| 2010/0056928 A1* | 3/2010 | Zuzak | .................. | A61B 5/0071 |
| | | | | 600/476 |
| 2011/0255745 A1* | 10/2011 | Hodder | ................ | G01N 21/359 |
| | | | | 382/103 |
| 2012/0190979 A1* | 7/2012 | McKenna | ................ | A61B 5/05 |
| | | | | 600/431 |

* cited by examiner

METHODS AND SYSTEMS USING LED SOURCES TO CREATE CONTRAST AGENTS FOR MID-INFRARED IMAGING OF BLOOD VESSELS

CROSS-REFERENCE TO RELATED APPLICATION

This application is a U.S. National Stage Entry Under 35 U.S.C. 371 of International Application No. PCT/US2015/017035 filed on Feb. 23, 2015, which claims the benefit of priority of U.S. Provisional Patent Application No. 61/919,971, filed on Dec. 23, 2013, and entitled "LED SOURCES TO CREATE CONTRAST AGENTS FOR MID-INFRARED IMAGING OF BLOOD VESSELS," the contents of which are incorporated in full by reference herein.

FIELD OF THE INVENTION

The present invention relates generally to the field of medical imaging and, in particular, to novel methods and systems for imaging vascular structures using thermal imaging.

BACKGROUND OF THE INVENTION

Current methods for thermal imaging (thermography) map gradients in body temperature, but do not map the detailed morphology of tissue structures. The present invention provides a method that maps vascular structures by selectively heating blood vessels relative to the surrounding tissue. This difference in temperature creates a contrast that allows such vessels to be seen in a thermal image. Surgical procedures that require vascular manipulation, such as aneurysm repair, tumor removal, and vascular malformation correction, would greatly benefit from the ability to visualize blood flow in vessels and their distribution beds during such procedures. To grow and progress, for example, solid tumors develop a complex vascular network. Mapping the morphology and function of tumor blood vessels is a potential biomarker of disease status. Further, accurate mapping of tumor vasculature can help delineate tumor margins during resection. The use of thermal imaging to detect tumor margins has been studied, as increased vascular density is associated with the presence of cancer tumors. The technique of the present invention provides accurate mapping of the locations of increased vascular density, and thus cancer tumor margins, by way of example.

Ultrasound is a common method used to map vessels. Standard ultrasound uses sound waves to penetrate soft tissue and then a probe measures the back-reflected wave from dense tissue (such as bone or muscle) to create an image. Doppler ultrasound uses the Doppler effect to measure and image blood flow. There are several types of Doppler systems, which vary in the way the acquired signal is processed and displayed. Ultrasound imaging is a non-invasive, cost effective imaging technique. However, ultrasound has relatively low resolution when compared to other techniques and requires a trained professional to analyze the captured images. Furthermore, ultrasound can produce real-time images, but uses a probe that must be in contact with the area being imaged. This limits its use in surgical techniques where a continuous real-time imaging of the surgical area is necessary.

Computed Tomography (CT) is also used to map the structure of blood vessels, but cannot be used to measure blood flow. CT scans are a series of X-ray images of the object being imaged. Many cross-sectional images are recorded as a scanner emits a narrow beam of X-rays while moving through an arc around the subject. The computer then assembles these 2D scans into a 3D rendering of the object being studied. The use of a helical path is currently being used to eliminate the gaps between cross-sections in standard simple arc scanners. This helical path allows the scanner to take continuous data and to increase the overall speed of the procedure. The images from these scans have excellent spatial resolution (~500 µm) and excellent penetration through soft tissues. However, there are significant limitations for use of this technique. Because the penetration depth for X-rays is about the same for all soft tissues, contrast agents are needed to distinguish between different soft tissue types in X-ray images. Many patients have allergic reactions to the intravenous contrast agents used to enhance the CT images. CT scans use ionizing radiation to produce images. X-rays are harmful to living tissue and exposure should be minimized when possible. Real-time CT imaging during a procedure is not possible due to the size and slow scanning speeds of the equipment.

Magnetic resonance imaging (MRI) is another method used to map the structure of blood vessels. Unlike CT scanning, MRI does not use X-rays. An MRI scanner uses a static magnetic field and radio waves to create detailed images of the body. MRI is particularly useful for tissues with many hydrogen nuclei and little density contrast, such as the brain, muscle, connective tissue, and most tumors. An MRI scanner creates a strong magnetic field and the protons in soft tissues become aligned with the direction of this external field. During MRI scans radio transmitters are used to broadcast radio frequency (RF) electromagnetic radiation into the body. These RF waves penetrate deeply into all tissue types because there is little absorption or scattering at these wavelengths. The aligned protons absorb a small amount of the RF signal and this flips the spin of the protons into an excited energy state. After the electromagnetic field is turned off, the spins of the protons become re-aligned with the static magnetic field. During this relaxation, a RF signal is generated. This outgoing RF signal is detected and is sent to a computer, which processes the signals into a 3D image of the area being examined. Protons in different tissues return to their equilibrium state at different rates and this effect is used to create contrast between different types of body tissue. MRI contrast agents alter the relaxation times of atoms within body tissues. MRI contrast agents are used to enhance the appearance of blood vessels, tumors, and inflammation. MRI has a good spatial resolution (<1 mm) and is capable of imaging different tissue types regardless of density. However, MRI cannot be used in real-time during a surgical procedure due to slow imaging speed, size of the equipment, and strong magnetic fields created by the scanner.

Optical coherence tomography (OCT) is a noninvasive, high spatial resolution method for imaging biological tissues. OCT is similar to ultrasound, except instead of sound waves, light is used to collect information about the subject. One type of OCT system uses a Michelson interferometer to create images of the subject. A broadband near-IR source is split into two beams; one focused on the subject and the other is used as a reference beam. The subject beam is used to scan the surface of the object being studied. When the subject beam is reflected off the subject it is passed through the interferometer where it is combined with the reference beam. This produces an interference pattern that is analyzed into an image. Doppler OCT combines standard OCT with laser Doppler flowmetry (LDF). LDF measures the frequency shift of light reflected off tissue structures to probe the speed and direction of the structures. By combining this with OCT, an image with excellent spatial resolution (~10 μm) and flow information can be created. OCT is limited to an imaging depth of 1 to 2 mm due to the absorption and scattering of the light used to probe the tissue. While OCT produces real time images, the field of view is small and the probe needs to be in close proximity to the patient, which can be obtrusive to the surgical team.

The scientific community is currently exploring new methods for imaging vasculature. One of the methods currently being investigated is optoacoustic, or photoacoustic, imaging. This method uses a train of optical pulses to produce a temperature change in tissue. This temperature change produces an acoustic wave caused by the thermoelastic change. This sound wave is then captured with a probe similar to an ultrasound probe. This technique has high spatial resolution. This method does not yet have the ability to map blood flow because the motion of the blood degrades the spatial resolution of the image. This technique also provides only a small field of view.

Thermal imaging allows the visualization of light in the 8 to 10 μm range of the electromagnetic spectrum. Thermal images are displayed as color maps that show variations in temperature of the objects being imaged. Mid-IR imaging is called thermography in medicine because the images obtained are maps of surface temperature as a function of position. Thermography has been used in medicine since the 1960's. It is an attractive imaging option because it is non-invasive and does not use ionizing radiation. Thermography has been used in such applications as the evaluation and treatment of burns and the diagnosis of superficial vascular disorders. In all of these applications, thermal imaging is used to find areas of tissue that experience an increase or decrease in tissue temperature. This temperature variation is the result of increased or decreased blood flow. The resulting images show temperature gradients across the tissue surface. A current limitation of thermography as a medical imaging tool is that the thermal images do not reveal the detailed structure of tissues.

Thermal imaging is a map of the mid-IR light emitted by tissue, so understanding the nature of this emission is necessary for properly interpreting these images. Thermal imaging of tissue treats the human body as a blackbody radiator. This means the tissue emits electromagnetic radiation at all frequencies according to Planck's Law (Equation 1).

$$I(\lambda, T) = \frac{2hc^2}{\lambda^5} \frac{1}{e^{\frac{hc}{\lambda kT}} - 1} \qquad \text{Equation 1}$$

$I(\lambda, T)$ is the intensity for a given wavelength and temperature, h is Planck's constant, c is the speed of light in a vacuum, $\lambda$ is the wavelength of the electromagnetic radiation, k is Boltzmann's constant, and T is the temperature of the body in Kelvin.

Blackbody emitters also follow Wien's Displacement Law (Equation 2).

$$\lambda_{max} = \frac{b}{T} \qquad \text{Equation 2}$$

where b is Wien's displacement constant ($2.897 \times 10^{-8}$ K·m) and T is the temperature of the body in Kelvin. Wien's law tells us the wavelength at which the blackbody emits the most energy. The human body at normal temperature (37.0° C.±0.5) emits light most strongly around 9.5 μm in the thermal IR. As a blackbody radiator gets hotter, the wavelength of peak emission will shift to shorter wavelengths.

The total energy radiated per unit surface area (irradiance, F) for a blackbody is described by the Stefan-Boltzmann Law (Equation 3).

$$F = \sigma T^4 \qquad \text{Equation 3}$$

where $\sigma$ is Stefan's Constant with a value of $$5.6704 * 10^{-8} \frac{J}{sm^2 K^4}$$

and T is the blackbody's temperature in Kelvin. The Stefan-Boltzmann law shows that as a blackbody radiator gets hotter, it will become brighter (greater irradiance).

FIG. 1 illustrates the differences between blackbody radiators of different temperatures. One object is at normal body temperature and the other is 100° C. warmer. Notice that the warmer object has a peak at a shorter wavelength and is brighter at all wavelengths.

BRIEF SUMMARY OF THE INVENTION

Recall that a current limitation of thermal imaging in medicine is that this technique does not provide detailed imaging of tissue structures, but rather a map of temperature changes across the tissue surface. For example, blood vessels and surrounding tissue are approximately the same temperature. This means that they emit about the same amount of mid-IR radiation and have about the same brightness in a thermal image. However, if one tissue's temperature is selectively altered compared to another, a contrast can be created in a thermal image that will allow discrimination of the tissue types. Hotter objects emit more energy, while cooler objects emit less energy. When viewed through a thermal imaging camera, warm objects stand out well against cooler backgrounds.

The present invention provides a technique to heat blood relative to surrounding tissue so that blood and blood vessels will look brighter than other tissue is a thermal image. A temperature contrast between blood vessels and the surrounding tissue can be achieved through selective heating of the blood, and thus the blood vessels. Hemoglobin absorbs light strongly at 420 nm and 530 nm. These hemoglobin absorption peaks lie inside the minimum for absorption by water, which is a primary component of soft tissue. If blood and tissue are irradiated with light with wavelength near 420 nm or 530 nm, the blood will heat up more than the surrounding soft tissue. This type of selective heating of blood is used routinely in laser treatments of vascular lesions, such as port wine stain. A laser with wavelength near the 530 nm blood absorption peak heats and coagulates blood vessels, while leaving surrounding water-rich tissue undamaged. The present invention uses a similar method to preferentially heat blood (without coagulating the blood or damaging the water-rich tissue) and thus provide a contrast agent for enhanced imaging. Note that one could cool the blood or surrounding tissue to achieve a contrast. However, cooling reduces blood flow and constricts blood vessels. The structure of small vessels cannot be accurately mapped using this type of technique.

The present invention uses LED light sources to selectively heat the blood, but a laser of the same wavelength could also be used.

The technique of the present invention, using thermal imaging to map vasculature, has potential applications in a wide range of medical procedures. For example, the ability to accurately map and monitor small vascular structures is invaluable during and after surgery to revascularize a trauma victim's limb or appendage. During the operation, the surgeon could use thermal imaging to locate and reattach any vasculature required to support proper circulation. The doctor could then monitor the region for leaks and immediately address these issues. During recovery, this imaging technique could be used to monitor circulation and allow for the early detection and correction of problems. Similar application of this imaging technique would be valuable in cardiac bypass surgery and any surgery requiring vascular manipulation. This imaging modality could be used to delineate the margins around solid mass tumors.

This technique provides medical professionals a real-time method for blood vessel mapping. The image created requires no special training to interpret and this imaging method has hands-free operation that increases its usability compared to other imaging methods.

In one exemplary embodiment, the present invention provides a method for imaging a vascular anatomical structure (blood vessels, blood, a tumor, etc.), comprising: selectively heating the vascular anatomical structure relative to an adjacent anatomical structure (tissue, etc.) by exposing the vascular anatomical structure to radiation using an optical source; imaging the heated vascular anatomical structure using a thermal imaging camera; and displaying the image on a display. The method also comprises processing the image using a spatial derivative analysis to find regions with steep spatial temperature gradients. The method further comprises processing the image using a temporal derivative analysis to find regions with rapid heating. The method still further comprises using the regions found to determine the margins of a solid mass tumor. The method still further comprises superimposing the margins of the solid mass tumor on another image of the solid mass tumor to provide a map for excising the solid mass tumor. The vascular anatomical structure is heated by about 0.5° C. relative to the adjacent anatomical structure. The optical source comprises a light emitting diode or a laser. The light emitting diode or the laser is operated in a pulsed mode or a continuous mode. The radiation has a wavelength of about 420 nm or about 530 nm. The thermal imaging camera is a mid-infrared thermal imaging camera.

In another exemplary embodiment, the present invention provides a system for imaging a vascular anatomical structure (blood vessels, blood, a tumor, etc.), comprising: an optical source for selectively heating the vascular anatomical structure relative to an adjacent anatomical structure (tissue, etc.) by exposing the vascular anatomical structure to radiation; a thermal imaging camera for imaging the heated vascular anatomical structure; and a display for displaying the image. The system also comprises a processor executing an algorithm for processing the image using a spatial derivative analysis to find regions with steep spatial temperature gradients. The system further comprises a processor executing an algorithm for processing the image using a temporal derivative analysis to find regions with rapid heating. The system still further comprises means for using the regions found to determine the margins of a solid mass tumor. The system still further comprises means for superimposing the margins of the solid mass tumor on another image of the solid mass tumor to provide a map for excising the solid mass tumor. The vascular anatomical structure is heated by about 0.5° C. relative to the adjacent anatomical structure. The optical source comprises a light emitting diode or a laser. The light emitting diode or the laser is operated in a pulsed mode or a continuous mode. The radiation has a wavelength of about 420 nm or about 530 nm. The thermal imaging camera is a mid-infrared thermal imaging camera.

BRIEF DESCRIPTION OF THE DRAWINGS

The present invention is illustrated and described herein with reference to the various drawings, in which.

DETAILED DESCRIPTION OF THE INVENTION

Figure 1:
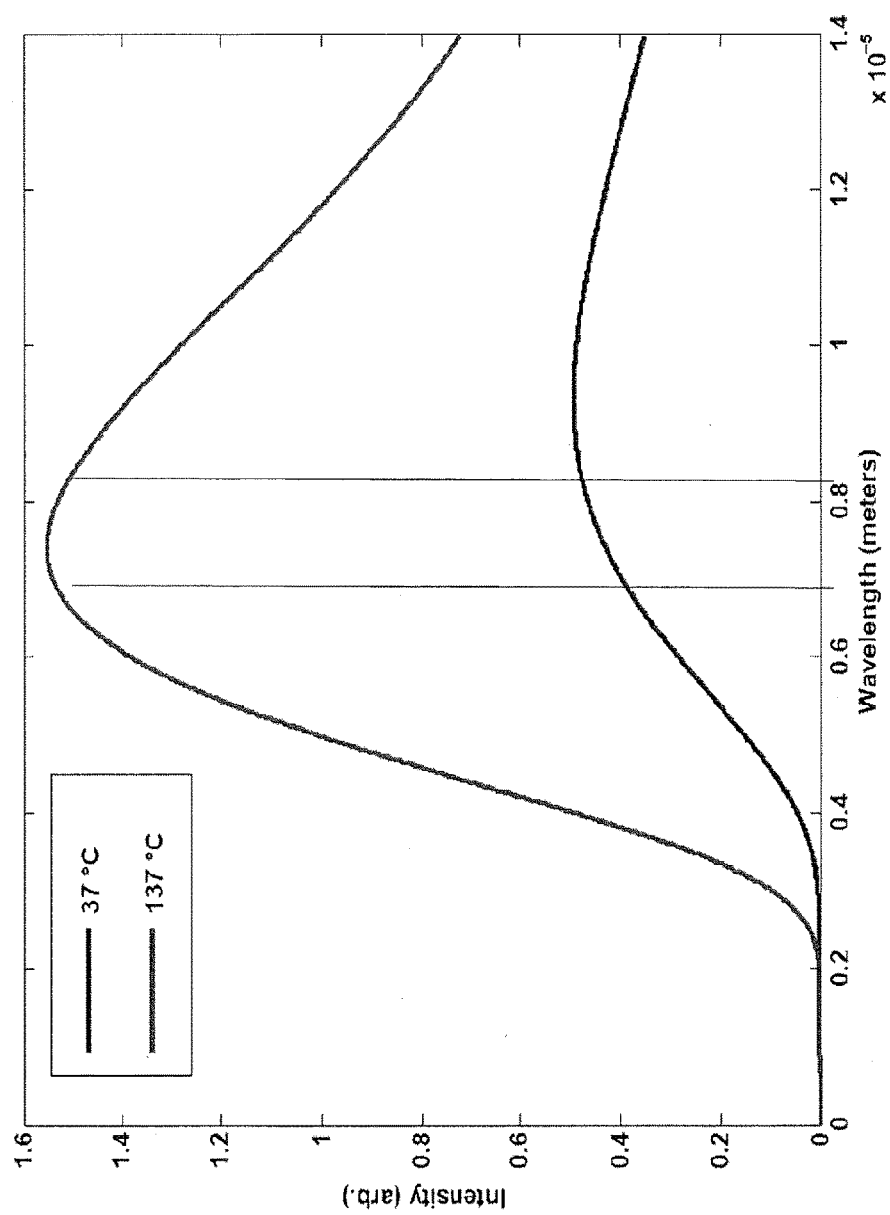
FIG. 1 is a plot illustrating blackbody curves for objects at two different temperatures; these curves show two objects separated by a 100° C. temperature difference; the warmer body has a peak emission at a shorter wavelength and a higher intensity than the cooler object; this is an exaggerated example of creating a contrast by heating one object with respect to another.
Figure 2:
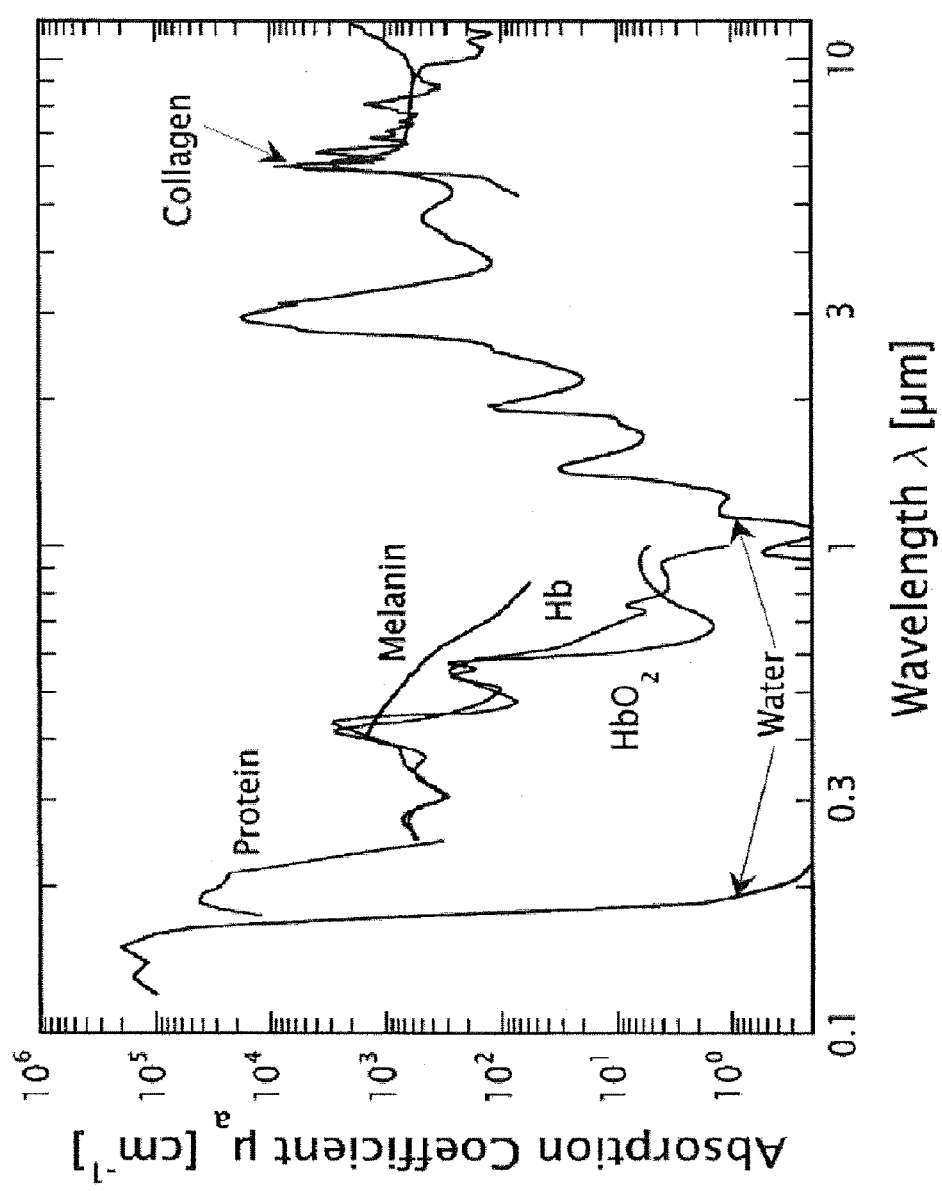
FIG. 2 is a plot illustrating absorption curves, showing the absorption peaks for oxygenated and non-oxygenated hemoglobin, protein, collagen, melanin, and water; note the location of the hemoglobin peaks near 420 and 530 nm; these absorption peaks lie inside a minimum for water absorption.
Figure 3:
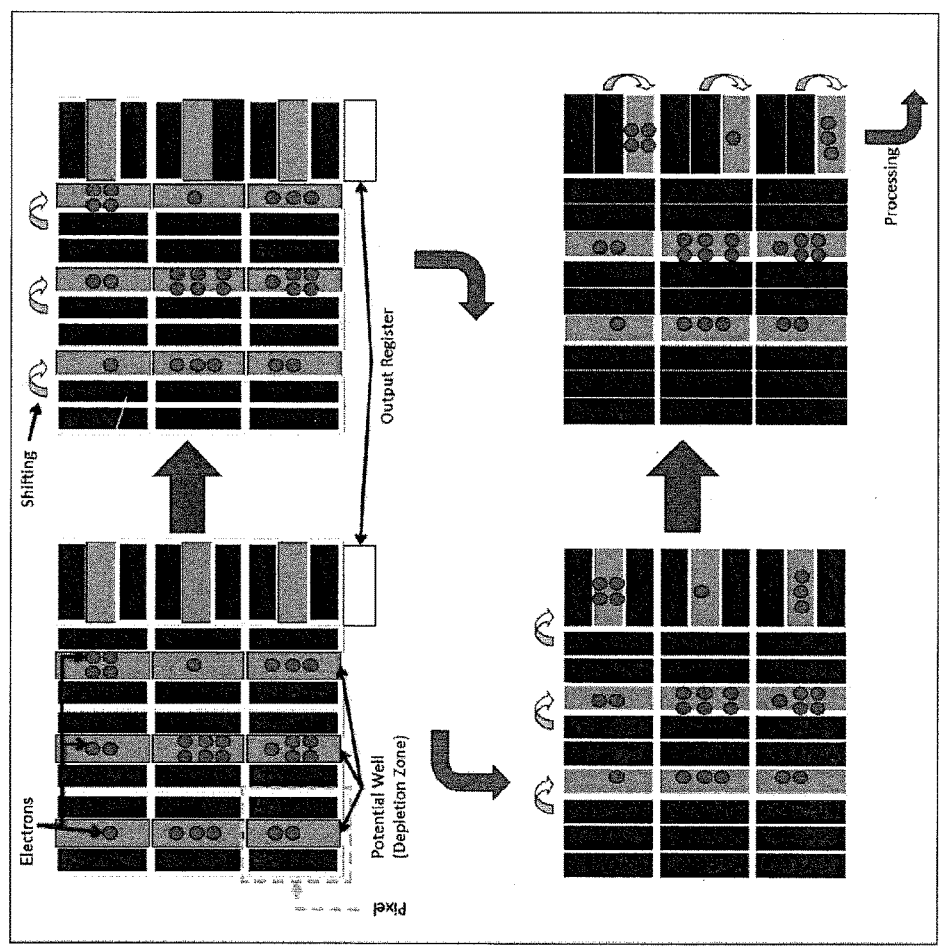
FIG. 3 is a schematic diagram illustrating CCD array charge collection and transport, depicting the function of a CCD array used for imaging; (from top left to bottom right) the charge is initially created by a photoelectric event is collected in the potential well of each CCD pixel; the charge is then shifted to the output register by altering the potential across the well (top right and bottom left); finally, the charge is moved to the processing electronics to create an image; the time required to complete this process is the maximum frame-rate of the CCD array.

IR imaging is a challenging task. The technology behind common detectors used at shorter wavelengths does not work in the mid-IR. Most imaging devices currently use charged-coupled devices (CCDs) as detectors. The principle behind a CCD device is best described with the analogy of rain falling on an array of buckets. In the initial stage, or charge collection stage, the buckets face upward collecting all rain that falls within their region. Any overflow represents the saturation of the detector. Once the collection period is completed, the buckets are moved down a belt to collect the rain into a trough to be measured. The amount of rain in each bucket is measured and this information is used to form an "image" of the rainfall over the entire array of buckets. The materials used in CCDs collect photons in the form of charges created via the photoelectric effect. These photoelectrons are captured in the potential well of the pixel on which the photon was incident. Once the collection period ends, the charges are sifted to a region called the output register (much like the trough in our analogy). The amount of change in each pixel is measures this information which is used to create an image. This is illustrated in FIG. 3.

CCDs rely on the photoelectric effect. If the incident photon does not have the necessary energy to eject an electron, a charge will not be available to be collected and thus no image can be created. The required energy of the photon is determined by the work function of the material, $\Phi=hf_0$, where h is Planck's constant and $f_0$ is the minimum, or threshold, frequency of the incident photon. The maximum kinetic energy, $K_{max}$, of the ejected electron is given by Equation 4.

$$K_{max} = hf - \Phi \quad \text{Equation 4}$$

when $K_{max} \leq 0$ the probability that an electron is ejected is zero (ignoring any special cases such as two-photon interactions). Mid-IR electromagnetic photons lack the energy to induce a photoelectric response in materials used in CCDs. This is the main reason these detectors are not available for IR imaging.

Figure 4:
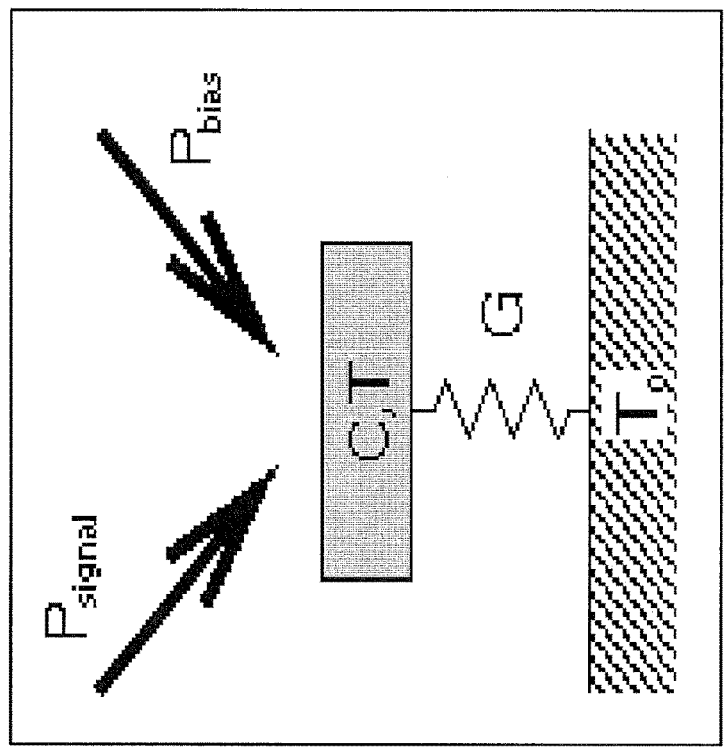
FIG. 4 is a schematic diagram illustrating a simple bolometer; power (Psignal) from an incident signal is absorbed by the bolometer and heats up a thermal mass with heat capacity (C) and temperature (T) and initial Power Bias (Pbias); the thermal mass is connected to a reservoir of constant temperature (T0) through a link of thermal conductance G; the temperature increase is $\Delta T=(Psignal+PBias)/G$; the change in temperature is measured with a resistive thermometer (thermistor)

IR imaging demands the use of another type of detector. These detectors are called bolometers or calorimeters. Bolometers measure a change in resistance that is related to the amount of energy absorbed by the thermal mass. Normally, these devices consist of a material of known heat capacity connected to a thermal reservoir by a resistor whose performance is well understood. The material is subject to an electrical bias and external radiation (or particles). As the heat absorbing material is exposed to incident radiation it experiences a change in temperature. This change is then measured by analyzing the change created in the electrical bias created by the varying value of resistance due to temperature change. This change in resistance follows the Steinhart-Hart equation for nonlinear temperature dependent resistance (Equation 5).

$$\frac{1}{T} = A + B \ln R + C \ln R^3 \quad \text{Equation 5}$$

where T is the temperature in Kelvin and R is the measured resistance in Ohms of the thermistor at T. A, B and C are the Steinhart-Hart coefficients which are a device property depending on the thermistor used. FIG. 4 (Berkeley 2001) shows a simplified layout of a single bolometer. In a thermal imaging system, many bolometers form an array where each bolometer acts as a pixel in the processed image. The camera used for this study is a FLIR SC600 series camera, which has a 640×320 array of microbolometers. It should be noted that a bolometer array is only a non-limiting example of a detector—there are new detectors coming on the market now that use different materials and function more like a CCD. The use of any such detector is contemplated herein.

It is important to point out that an IR camera using bolometers does not measure the temperature of an object directly. The measurement comes from the collection of infrared electromagnetic waves that can either be emitted or reflected off of the body. Emissivity ($\varepsilon$) is a property of the material being study. Assuming that an object has no transmittance, emissivity is the fractional amount of incident light that is emitted compared to the amount reflected (known as reflectance (R)). Equation 6 shows the relationship between $\varepsilon$ and R.

$$1 = \varepsilon + R \quad \text{Equation 6}$$

This relationship shows that as $\varepsilon$ increases, R must decrease at the same rate. As previously stated, the human body is treated as a perfect blackbody. This means that the emissivity is approximated to be 1 and the reflectance to be 0. This assumes that the signal from the tissues will contain no reflected signal and be composed of only emission from the object being studied. The emissivity of the human body is known to be approximately unity in the mid-IR (see Table 1; Lahiri et al. 2012).

TABLE 1

Emissivity of various human tissues as 40° C. in infrared wavelengths.

| Tissue | Emissivity |
|---|---|
| Black Skin (3-12 µm) | 0.98 ± 0.01 |
| White Skin (3-12 µm) | 0.97 ± 0.02 |
| Burnt Skin (3-12 µm) | 0.97 ± 0.02 |
| Pericardium (9 µm) | 0.95 |

The present invention was designed to selectively heat blood in order to induce a contrast in a thermal image allowing the mapping of blood vessels for medical applications. The first set of studies tested the response of different tissue types to LED sources with wavelengths of 405 nm and 530 nm. The second set of studies tested the selective heating of blood that was flowing through tissue.

A FLIR SC600 series mid-IR camera was used to record temperature changes in tissue samples as they were exposed to the different LED sources. The camera has a maximum pixel resolution of 640×480 and a maximum frame rate of 200 fps. The camera is sensitive from 7.5 to 14.0 microns making it ideal for the detection of body temperature sources.

Figure 12:
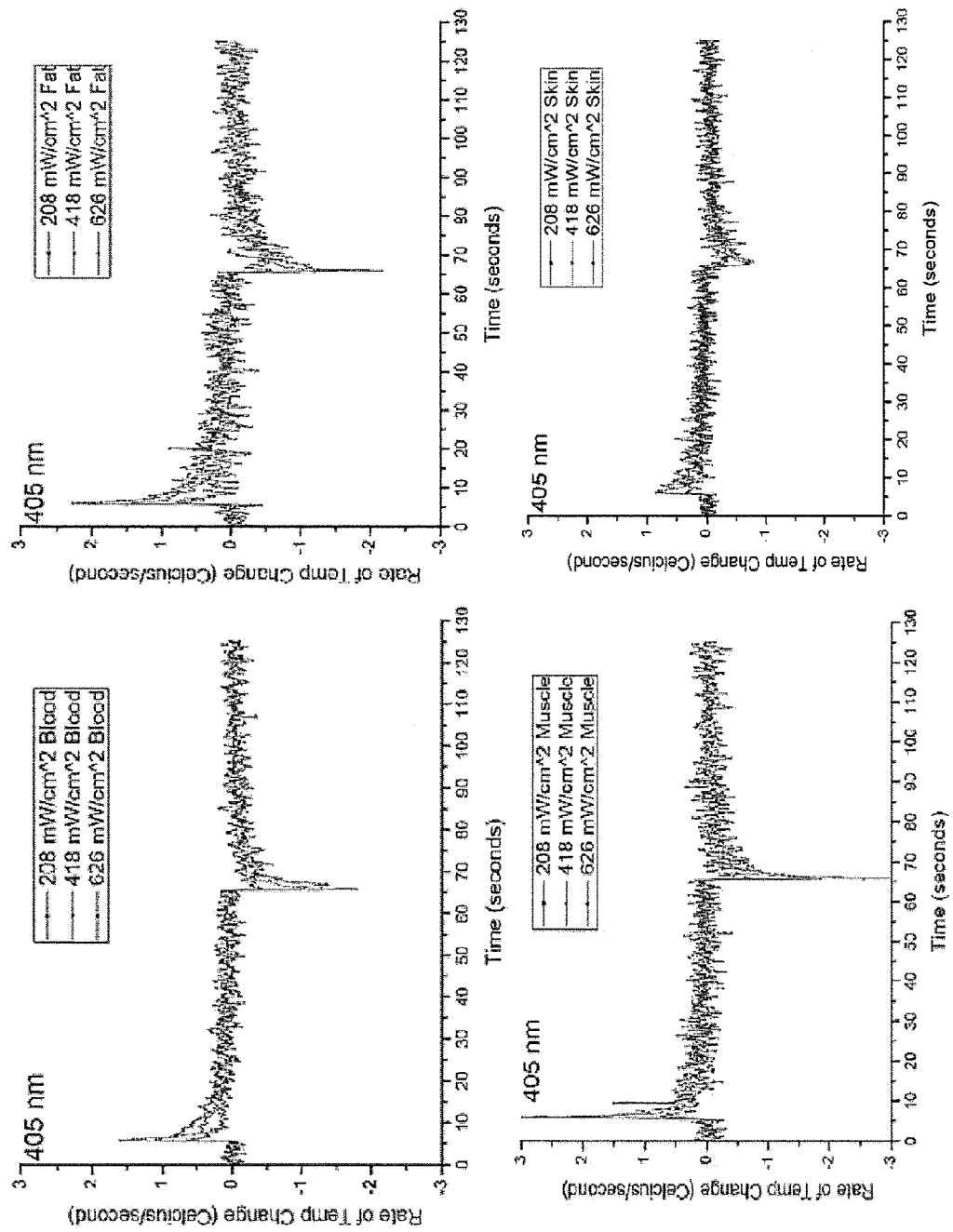
FIG. 12 is a series of plots illustrating rate of temperature change for 405 nm; these plots show the rate of change for the previous plots (ΔT/Δt); the positive values represent a heating event while the negative values represent a cooling event; the large spikes signify the beginning and end of illumination; note that the heating rates for all tissue types are significant.

The LED sources operated with peak wavelengths of 405 nm (Thorlabs M405L2) and 530 nm (Thorlabs M530L2) and maximum power outputs of 1500 and 1000 mW, respectively (see FIG. 12). The LED's were controlled using a high power LED driver (Thorlabs DC2100). (See FIG. 5).

Figure 5:
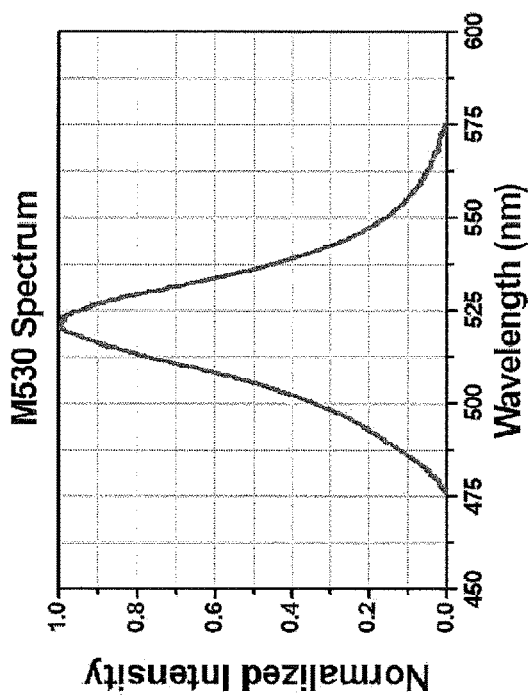
FIG. 5 is a 405 nm LED spectrum plot showing a normalized emission spectrum and a 530 nm LED spectrum plot showing a normalized emission spectrum.
Figure 5:
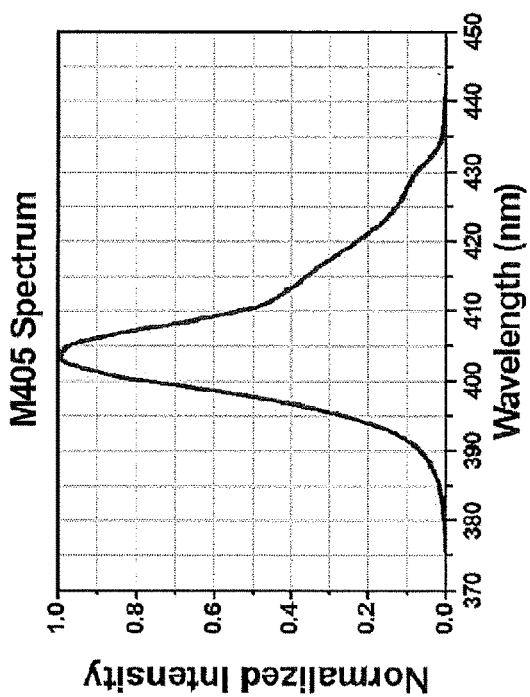

FIG. 5 shows the spectra for the LEDs. The 405 nm and 530 nm LED sources have spectral widths of 12 nm and 16 nm, respectively. Laser diode sources at 405 nm and 530 nm have narrower spectral widths (approximately 5 nm). This difference in spectral width is not an issue for this study. We are trying to illuminate tissue with light that is of the same wavelength as the hemoglobin peaks. These peaks are broad (>20 nm) and are well matched by the LED sources. The low cost and reliability of the LED's make these sources an attractive alternative to more expensive, higher-maintenance laser sources.

The LEDs were factory collimated to a beam width of 35 mm and then focused to a 2.5 mm spot using a single biconvex lens. Razor blade scans were conducted to determine the profile and spot size of the LEDs. This was accomplished by using a micrometer stage to move a slit made with two razor blades over the detection surface of a power meter (see FIG. 6). Scans were made along orthogonal axes to show the profile across each direction of the LED spot.

The razor blade scans were conducted at varying power densities ranging from $$208 \frac{mW}{cm^2} \text{ to } 3840 \frac{mW}{cm^2}.$$

Figure 6:
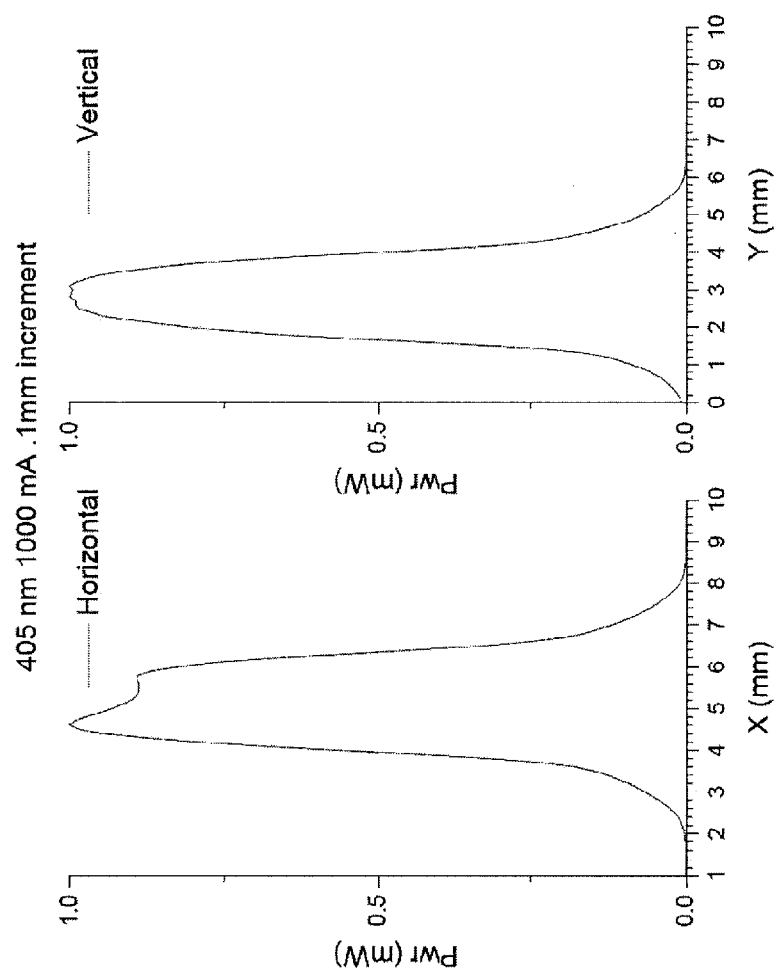
FIG. 6 is plots illustrating a razor blade scan of a 450 nm LED at 3.84 W/m$^2$; the razor blade scan was used to find the beam profile of the 405 nm LED; scans were made along orthogonal axes to show the profile across each direction of the LED spot, the irregularity seen in the 0 degree plot is a true artifact of the manufacturing of the LED, but had no adverse effect on these studies.

FIG. 6 is a normalized plot of one of these scans. The profile for the 405 nm LED remained the same for each of the tested power densities. The test was conducted a second time to verify the presence of the irregularity in the peak of the zero degree scan. The dip near the peak is an artifact of the LED's production. By analyzing the temperature profile across the LED spot, we determined that heating was unaffected by this aberration. The spot size was measured to have a FWHM of 2.5 mm. The scans of the 530 nm LED showed no aberration near the peak and also had a FWHM spot size of 2.5 mm.

Figure 7:
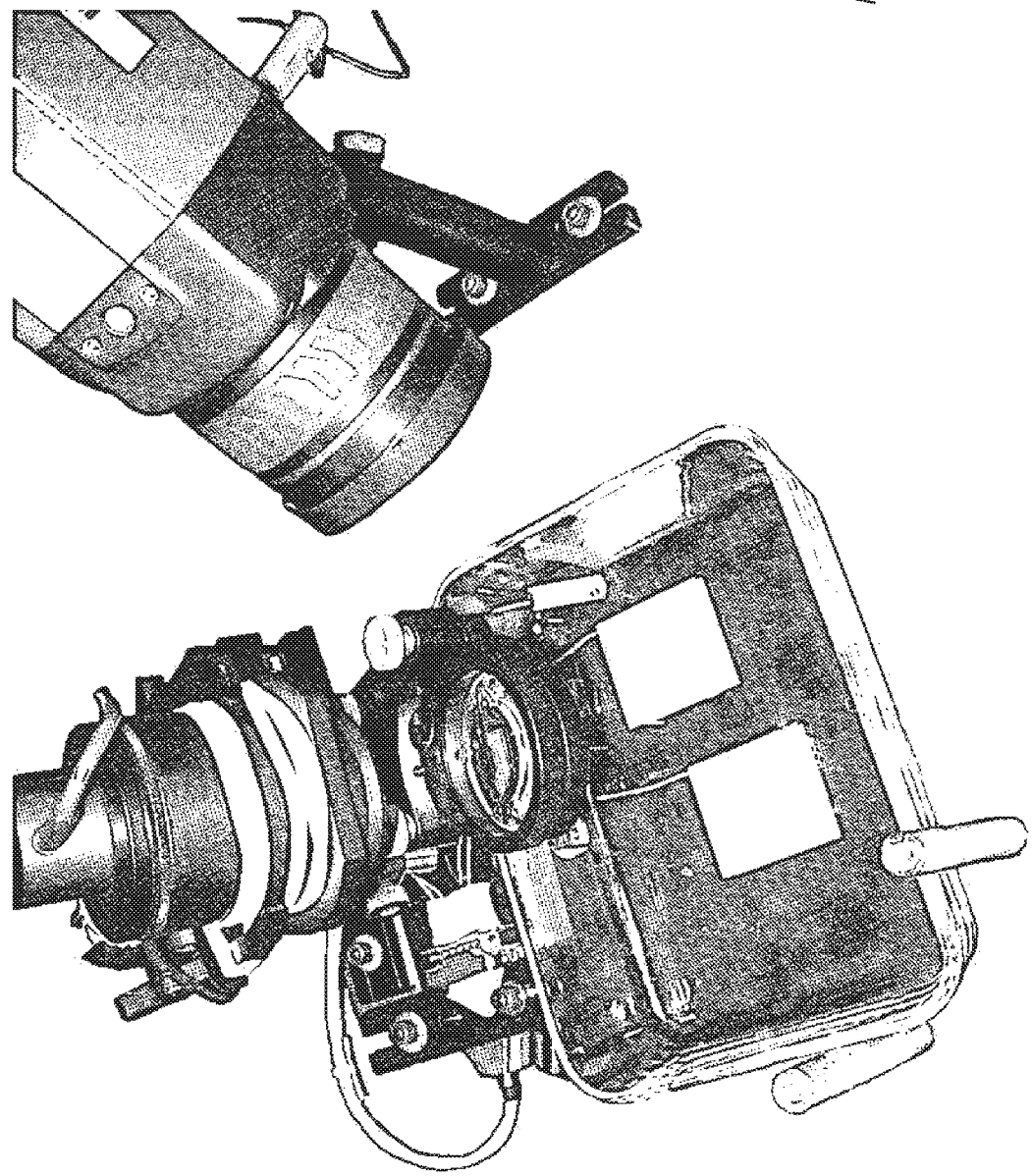
FIG. 7 is a photograph illustrating the tissue testing apparatus consisting of collimated LED sources focused to the desired spot size with a biconvex lens, a Pyrex dish placed on two thermoelectric heaters with a thermistor for temperature feedback, and a FLIR SC 600 series camera.
Figure 8:
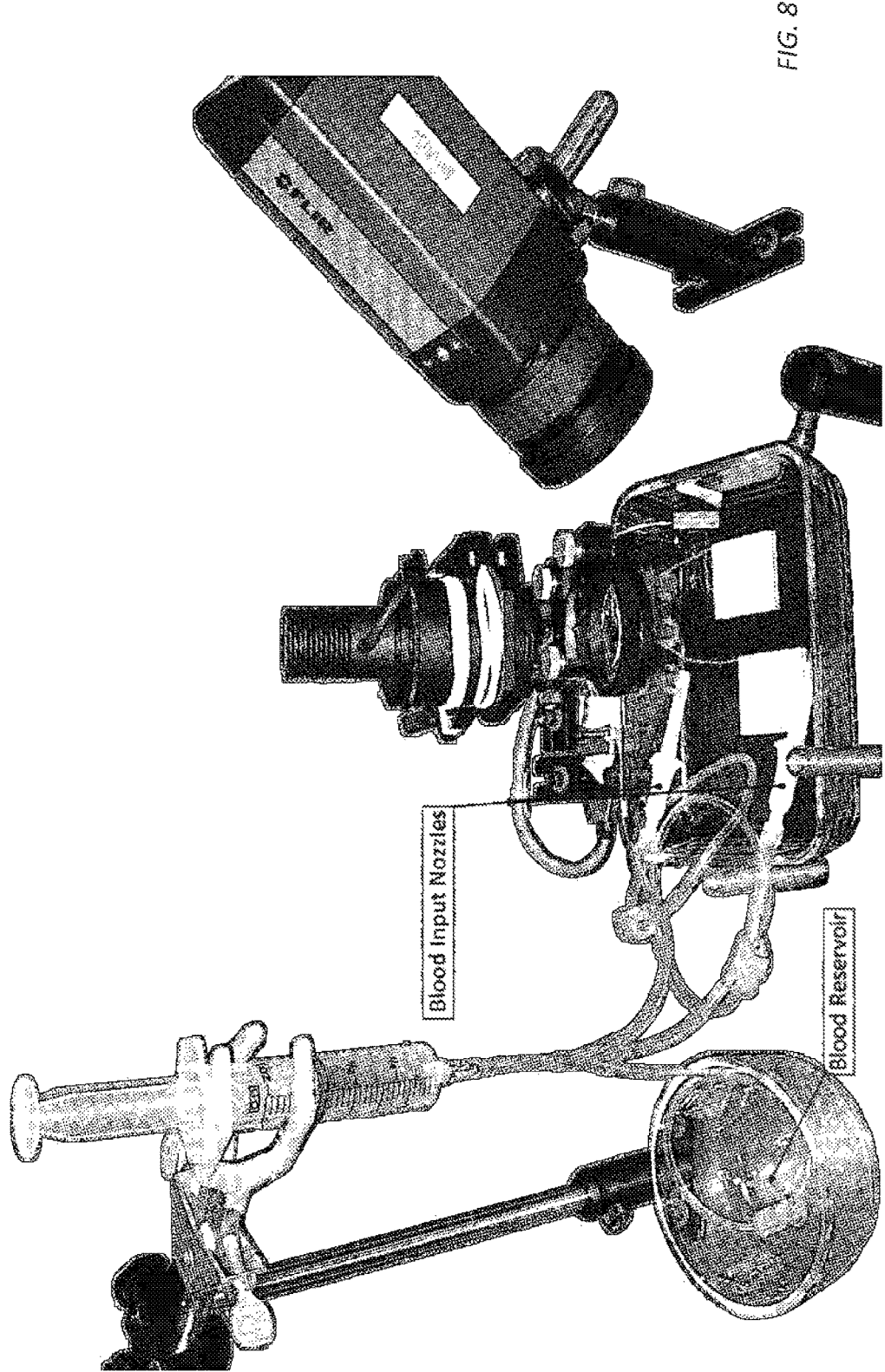
FIG. 8 is a photograph illustrating the testing apparatus with flow system installed, including all the components used in the flow test including the FLIR SC 600 series camera, collimated LED source, and the flow system itself.

FIG. 7 is a photograph illustrating the issue testing apparatus consisting of collimated LED sources focused to the desired spot size with a biconvex lens, a Pyrex dish placed on two thermoelectric heaters with a thermistor for temperature feedback, and a FLIR SC 600 series camera.

We studied whole blood, heart muscle, skin (epidermis and dermis), and fat samples from porcine donors. Porcine tissue was used due to its similarity to human tissues. Tissues were obtained from Animal Technologies, Inc. (Tyler, Tex.). The blood was collected from donors sacrificed on the day of shipment and contained EDTA anticoagulant to prevent clotting. The blood was stored at approximately 5°

C. in a refrigerator. Upon arrival the tissue was segmented into approximately 1" by 1" pieces, individually packaged, labeled, and frozen. The tissue types used in this study have known optical properties at the wavelengths studied. (See Table 2).

TABLE 2

Tissue Optical Properties. The absorption coefficients for blood at 405 nm and 530 nm are larger than those of the other tissues studied. This is the mechanism that will be used to selectively heat blood.

| Tissue | Wavelength (nm) | Absorption $\mu_a$ (mm$^{-1}$) | Scattering $\mu_s$ (mm$^{-1}$) |
|---|---|---|---|
| Epidermis | 405 | 1.28 | 52.2 |
|  | 530 | 0.56 | 31.25 |
| Dermis | 405 | 0.9 | 37.35 |
|  | 530 | 0.28 | 20.2 |
| Blood | 415 | 300 | 48 |
|  | 532 | 26.6 | 47.3 |
| Subcutaneous Fat | 405 | 1.67 | 24.35 |
|  | 530 | 0.41 | 16.1 |
| Muscle | 405 | 13 | 50.6 |
|  | 530 | 14.8 | 28.5 |

During all the tests, tissue samples were maintained near internal body temperature (37.5° C.) in a saline bath held at constant temperature by a pair of Peltier dishes.

The purpose of these tests was to evaluate the heating of tissue exposed to 405 nm and 530 nm LEDs as a function of time. The first study conducted involved the testing of the tissue types individually (except for dermis and epidermis, which were conducted together). Prior to testing, the tissue was thawed in a warm water bath. Once thawed, the samples were placed in the saline bath and heated to body temperature. The LED was positioned to provide a spot with a 2.5 mm radius on the tissue surface and the thermal camera was focused to the surface of the tissue at the LED spot location. The temperature of the tissue was monitored by recording a video with the thermal camera as the tissue was illuminated with the LED. This video was recorded at a frame rate of approximately 50 fps. To obtain a baseline temperature measurement, the video began 5 seconds before LED illumination. The LED then illuminated the tissue surface for 60 seconds. Recording continued for 60 seconds after the LED was turned off to monitor the cooling of the tissue sample. Five data sets were collected for each power density/tissue combination. This was performed for each tissue type with both the 405 nm and 530 nm LEDs and at several different LED power densities (see Table 3). The spot size was held constant for all tests and the power density was adjusted by controlling the input current of the LEDs.

The heating response of the whole blood was evaluated on the day the tissue and blood arrived in the lab. Prior to each test, a small amount of the whole blood was exposed to the LED and the heating response was measured. This response was then compared to the repose of the blood on the first day to make sure that the response did not degrade over time. The blood maintained the same response for about 2.5 weeks. The other tissues were frozen to preserve them during the two weeks of testing. Freezing tissues is known to be an acceptable method for preservation.

TABLE 3

Experiments completed for tissue tests.

| Tissue Type | Power Density (W/cm$^2$) | LED Wavelength (nm) | Spot Diameter (mm) | Sample Size (n) |
|---|---|---|---|---|
| Fat | 208 | 405 | 2.5 | 5 |
| Fat | 418 | 405 | 2.5 | 5 |
| Fat | 626 | 405 | 2.5 | 5 |
| Muscle | 208 | 405 | 2.5 | 5 |
| Muscle | 418 | 405 | 2.5 | 5 |
| Muscle | 626 | 405 | 2.5 | 5 |
| Skin | 208 | 405 | 2.5 | 5 |
| Skin | 418 | 405 | 2.5 | 5 |
| Skin | 626 | 405 | 2.5 | 5 |
| Blood | 208 | 405 | 2.5 | 5 |
| Blood | 418 | 405 | 2.5 | 5 |
| Blood | 626 | 405 | 2.5 | 5 |
| Fat | 208 | 530 | 2.5 | 5 |
| Fat | 418 | 530 | 2.5 | 5 |
| Fat | 626 | 530 | 2.5 | 5 |
| Fat | 886 | 530 | 2.5 | 5 |
| Muscle | 208 | 530 | 2.5 | 5 |
| Muscle | 418 | 530 | 2.5 | 5 |
| Muscle | 626 | 530 | 2.5 | 5 |
| Muscle | 886 | 530 | 2.5 | 5 |
| Skin | 208 | 530 | 2.5 | 5 |
| Skin | 418 | 530 | 2.5 | 5 |
| Skin | 626 | 530 | 2.5 | 5 |
| Skin | 886 | 530 | 2.5 | 5 |
| Blood | 208 | 530 | 2.5 | 5 |
| Blood | 418 | 530 | 2.5 | 5 |
| Blood | 626 | 530 | 2.5 | 5 |
| Blood | 886 | 530 | 2.5 | 5 |

The second study conducted simulated the flow of blood through blood vessels. A whole porcine heart, of approximate human size, was used in the test. An IV like setup with a hypodermic needle was used to introduce blood flow into the existing vasculature in a segment of porcine heart tissue. The vessel used for the introduction of blood was chosen by visual inspection. This vessel was at the surface of the tissue near the LED spot and remained near the surface for 3 cm. Beyond the initial 3 cm the blood vessel was below the surface of the heart muscle tissue and could not be seen by visual inspection. Before the blood was introduced, the vessels were flushed with saline to clear the vessels of any obstructions.

The LED illuminated the vessel a short distance from the end of the needle. The blood was heated as it flowed through the LED spot and then this heated blood continued to flow through the vascular network. The flow of this warmed blood through the vascular network was monitored with the thermal camera for 120 s after the introduction of blood into the vessel. Tests were conducted with both the 405 nm and 530 nm LEDs with irradiances of 3840 mW/cm$^2$ and 680 mW/cm$^2$, respectively. These tests were completed at the maximum output of each LED to test the methodology. Tissue damage thresholds were not considered and will be a subject of future studies. Experiments were conducted using both continuous and pulsed LED illumination. During one set of tests, the LED was on for 5 s and then off for 5 s, while in the other series of tests the LED was on for 10 s and off for 10 s. Table 4 summarizes the experimental parameters used for the simulated blood flow tests.

TABLE 4

Experimental parameters used for the simulated blood flow tests

| Wavelength (nm): | 405 | 530 |
|---|---|---|
| Irradiance (mW/cm$^2$): | 3840 | 680 |

TABLE 4-continued

Experimental parameters used for the simulated blood flow tests

| Spot Diameter (mm): | 5 | 5 |
|---|---|---|
| Mode of LED Illumination[a] | Continuous 5 s pulsed 10 s pulsed | Continuous 5 s pulsed 10 s pulsed |

The data output of our experiments consisted of videos that recorded the change in temperature as a function of time and a function of position on a tissue sample. We analyzed each experiment (a particular tissue type illuminated by a particular LED at a given power) separately. For all experiments, we examined a region of interest (ROI) in each video for analysis using FLIR ExaminerIR software package. The ROI was defined to be the region of the tissue illuminated by the LED (LED spot). For each video, temperature versus time was plotted. The average temperature of the first 5 seconds of the video (no LED illumination) was taken to be the initial temperature of the sample. We determined the change in temperature as a function of time, ΔT, by subtracting the initial temperature from the average temperature of the ROI. We repeated each experiment (tissue at a given power with a particular LED) multiple times. We averaged these multiple runs to get ΔT versus time for each tissue type at each power. This information was exported to Origin Pro to plot ΔT versus time to display how the tissue was heated in response to LED illumination (see FIGS. 9 and 10). We repeated this process for all experiments.

Figure 9:
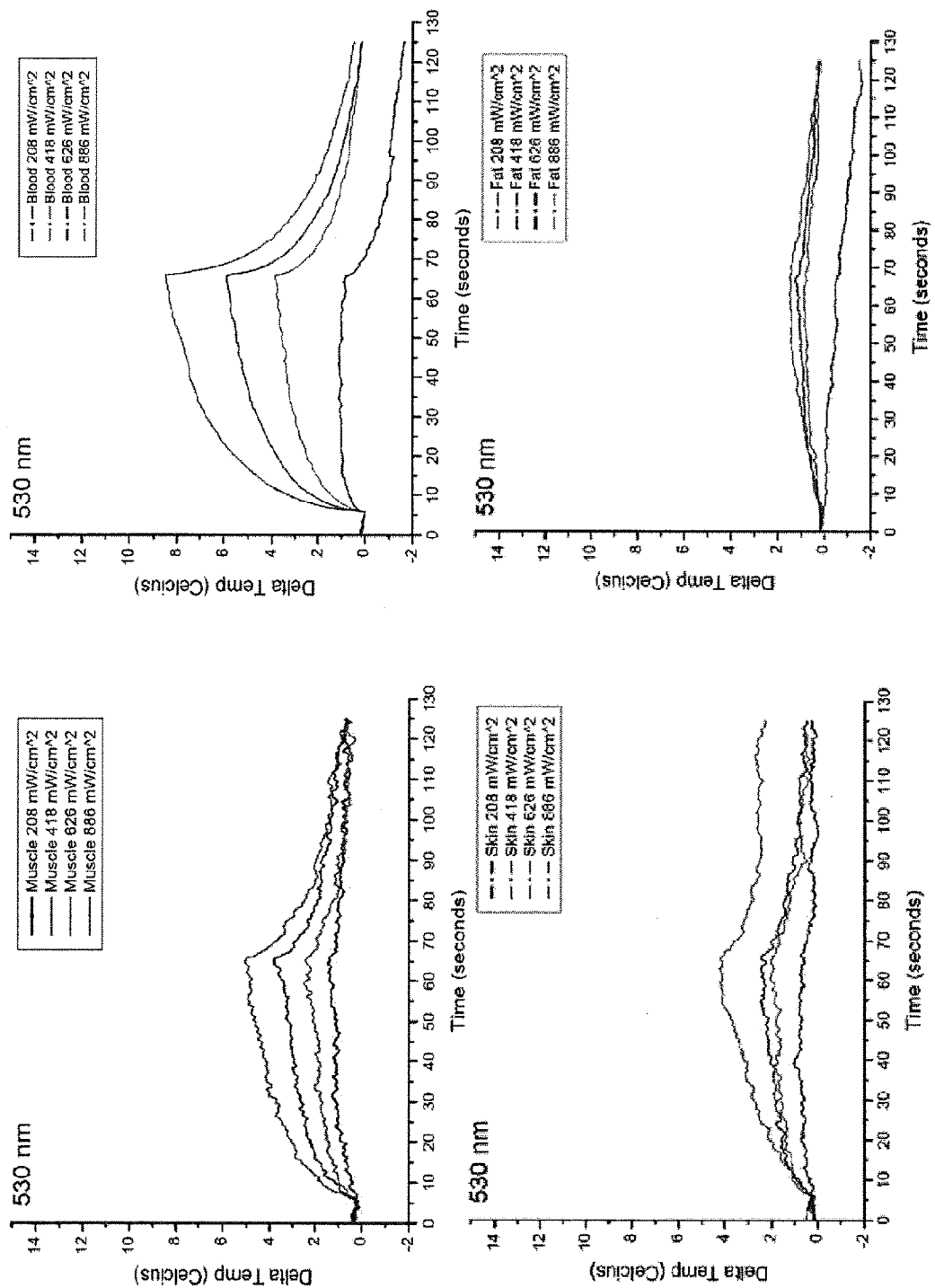
FIG. 9 is a series of plots illustrating change in temperature for illumination with the 530 nm LED; these plots show the change in temperature over the entire recorded video; the first 5 seconds is indicates the initial temperature of the tissue sample; from 5 to 65 seconds the tissue was illuminated by the LED source; the remaining 60 seconds shows the behavior of the tissue as it cools; notice that the change in temperature for blood is the largest of all tissue types; also notice that the slope of the heating curve for blood is stepper than the other curves; the standard deviation from the mean ΔT for each experiment was approximately 0.5° C.
Figure 10:
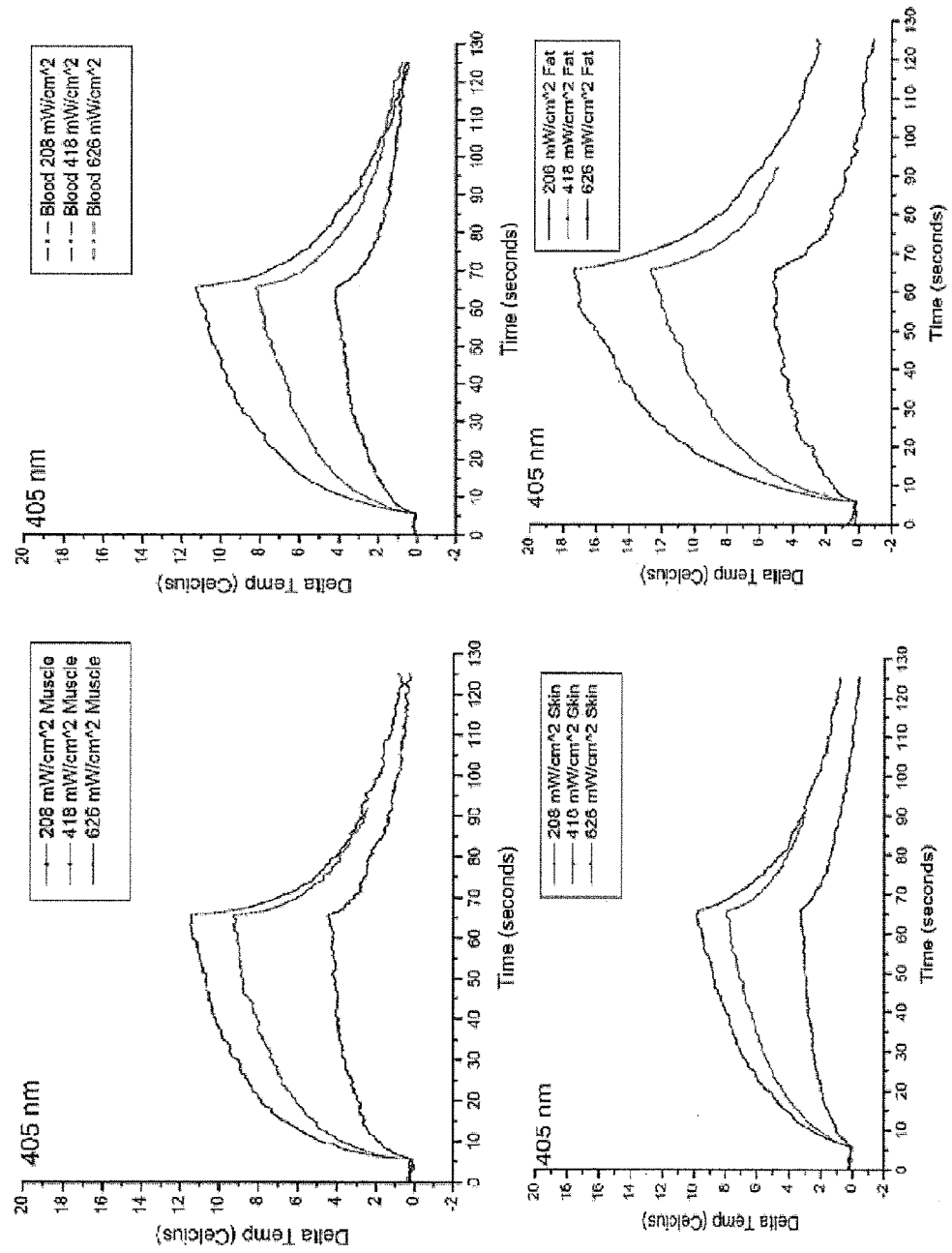
FIG. 10 is a series of plots illustrating change in temperature for illumination with the 405 nm LED; these plots show the change in temperature over the entire recorded video; the first 5 seconds indicates the initial temperature of the tissue sample; from 5 to 65 seconds the tissue was illuminated by the LED source; the remaining 60 seconds shows the behavior of the tissue as it cools; notice that fat, not blood, shows the largest temperature rise; this is likely due to convective cooling of the blood during these experiments; the standard deviation from the mean ΔT for each experiment was approximately 0.5° C.

FIGS. 9 and 10 show the change in temperature versus time for all tissue types and at all powers used. The standard deviation from the mean ΔT for each experiment was measured to be approximately 0.5° C. As expected, the greater the incident power, the greater the change in the temperature of the tissue for both the 405 nm and 530 nm LEDs.

The tests with the 530 nm LED yielded interesting results. In the experiments in which the tissue was illuminated with the 530 nm LED, the blood heated more (reached a higher ΔT) than the other tissue types at a given power. This shows that selectively heating the blood relative to water-rich tissue with the 530 nm LED is possible. Also, notice that the slope of the ΔT versus time graph is steepest for blood. This means that the blood is heating more quickly than the other tissue types when illuminated with 530 nm light. The results of the 530 nm tests agree with our expectations based on the absorption coefficients. Blood has a larger absorption coefficient than the other tissue types that we tested at 530 nm. This means the 530 nm light will deposit more energy in a volume of blood than other tissues. Consequently, blood should heat more than other tissues when exposed to 530 nm light. The blood does experience the largest change in temperature in our experiments.

All of the tissue types are heated more (at a given power) when illuminated with the 405 nm LED compared to illumination with the 530 nm LED. However, at 405 nm the blood heated slightly more than skin, but significantly less than fat in our experiments. The heating of blood was comparable to the temperature increase in muscle. These results were not expected. The absorption coefficient for blood is significantly higher at this wavelength than for other tissue types. A large absorption coefficient means that a large amount of energy will be deposited in the tissue per cm. The blood should heat more than the other tissue types upon illumination with the 405 nm LED. The power densities, spot size and duration of illumination were all the same in the tests with the 405 nm and 530 nm LEDs.

Fat heated significantly more than blood (ΔT of 17° C. for fat versus 11° C. for blood) when illuminated with the 405 nm LED even though the absorption coefficient of blood is 180 times larger than the absorption coefficient for fat at this wavelength. It is unlikely that the absorption coefficients are wrong by such a large factor. It is more likely that energy is being deposited into the blood by the 405 nm LED and causing a temperature rise, but we do not measure this with the thermal camera. Energy is transferred by three mechanisms: radiation, conduction, and convection. The thermal camera is sensitive to radiative emission (see discussion of blackbodies). Conduction is likely transferring the same amount of energy away from the LED spot in both the 405 nm and 530 nm experiments. The ROI for the heated region in the 405 nm and 530 nm experiments was the same. This indicates that conduction (seen as thermal blooming) played an equal role in energy transfer in both experiments. Convection is an important energy transfer mechanism in gases and liquids. The surfaces of all tissue samples were exposed to air during the experiments. Convective energy transfer likely plays a significant role at the interface between the heated blood and the room temperature air. Heat transfer via convection can be described by Equation 7.

$$q = h_c A dT \qquad \text{Equation 7}$$

where q is the heat transfer per unit time, A is the surface area of the heated spot on the tissue, $h_c$ is the convection coefficient (in this case it would be for air), and dT is the difference in temperature between the air and the heated blood. For the 405 nm and 530 nm experiments $h_c$ and A are the same. If the temperature rise in the blood was really higher in the 405 nm experiments than the 530 nm experiments, we would expect that convection would be an important heat loss mechanism in these experiments. Energy would be transferred away from the heated spot via convection implying that the tissue could have heated more than we measured with the thermal camera. We have experiments planned to test the importance of convective cooling. Convective cooling will not be a problem for blood flowing through blood vessels, as the blood is not in contact with the surrounding air.

Figure 11:
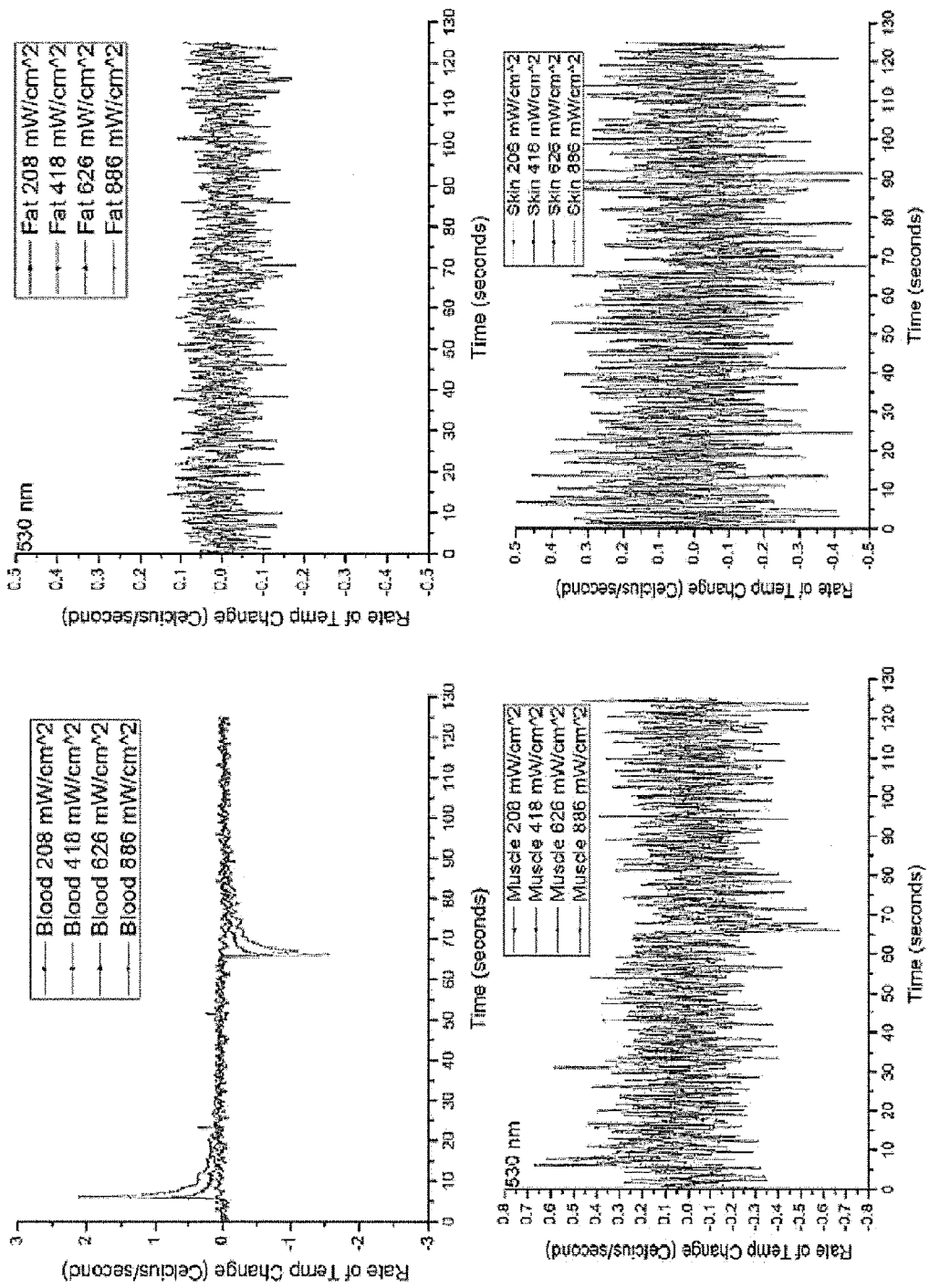
FIG. 11 is a series of plots illustrating rate of temperature change for 530 nm; these plots show the rate of change for the previous plots (ΔT/Δt); the positive values represent a heating event while the negative values represent a cooling event; the large spikes signify the beginning and end of illumination; note that the blood is the only tissue type to show a significant response when illuminated by the 530 nm LED.

The most interesting result of the individual tissue testing involves the heating rates of the tissue samples. The heating rate (the slope of the curves shown) is larger for blood than other tissue types. This is especially noticeable for the 530 nm LED tests. Blood heats much more rapidly than skin and fat and slightly faster than muscle. We calculated the time derivative for the ΔT versus time plots using the derivative function in Origin Pro 8. FIGS. 11 and 12 show the results of this calculation for the 530 nm and 450 nm LEDs incident on blood, muscle, fat, and skin at power densities ranging from 208 W/cm² to a maximum of 886 W/cm² for 530 nm and 626 W/cm² for 405 nm. For 530 nm this clearly shows that the blood heats most quickly and that the heating rate is almost constant for other tissue types. The heating rate drops dramatically soon after illumination begins. This suggests that pulsed LED illumination would result in the most dramatic heating response in blood relative to other tissue types. The 405 nm results are not as clear. The blood has a rate of change comparable to the 530 nm test but the other tissues also experience large rates of change. The 405 nm experiments were affected by convective cooling.

The goal of these studies was to image warm blood as it flowed through the vascular structure of a porcine heart. Blood was injected using a syringe and then this blood flowed under the LED spot where it was heated. This warm blood flowed through the vasculature. The 405 nm LED was tested for this preliminary study. The 530 nm LED was not tested due to a lack of tissue samples, but will be tested in a future study. Our tissue tests showed that the most significant heating response was experienced by tissue immediately after exposure to the LED. In these flow tests, the LED was pulsed at 1 Hz, 0.2 Hz and 0.1 Hz cycles for each test. Continuous LEDs could also be used.

The videos from the tests were exported frame by frame as CSV files, using ExaminerIR. Matlab R2010a was then used to process these images. A 2D adaptive noise filter included in the Matlab image processing tool kit called Wiener2 was applied to the raw frames. This method uses a linear filter that is adapted on a pixel by pixel basis. This noise reduction method allows the smoothing to be greater where little variance in the original image is seen and less where larger variance is seen. This allows the background (region of little change) to be directly targeted by the filter. Since our goal is to clearly see changes in the thermal image this method was adopted. The Wiener2 method estimates the local mean (Equation 8) and standard deviation (Equation 9) for a N×M neighborhood around each pixel of the image where η is the neighborhood of each pixel in the image.

$$\mu = \frac{1}{NM} \sum_{n_1, n_2 \in \eta} a(n_1, n_2) \qquad \text{Equation 8}$$

$$\sigma^2 = \frac{1}{NM} \sum_{n_1, n_2 \in \eta} a^2(n_1, n_2) - \mu^2 \qquad \text{Equation 9}$$

These estimates are then used to create a pixel-wise Wiener filter given by Equation 10.

$$b(n_1, n_2) = \mu + \frac{\sigma^2 - v^2}{\sigma^2}(a(n_1, n_2) - \mu) \qquad \text{Equation 10}$$

where $v^2$ is the noise variance. The Wiener2 function used an average of all the locally estimated variances for the entire frame.

Figure 13:
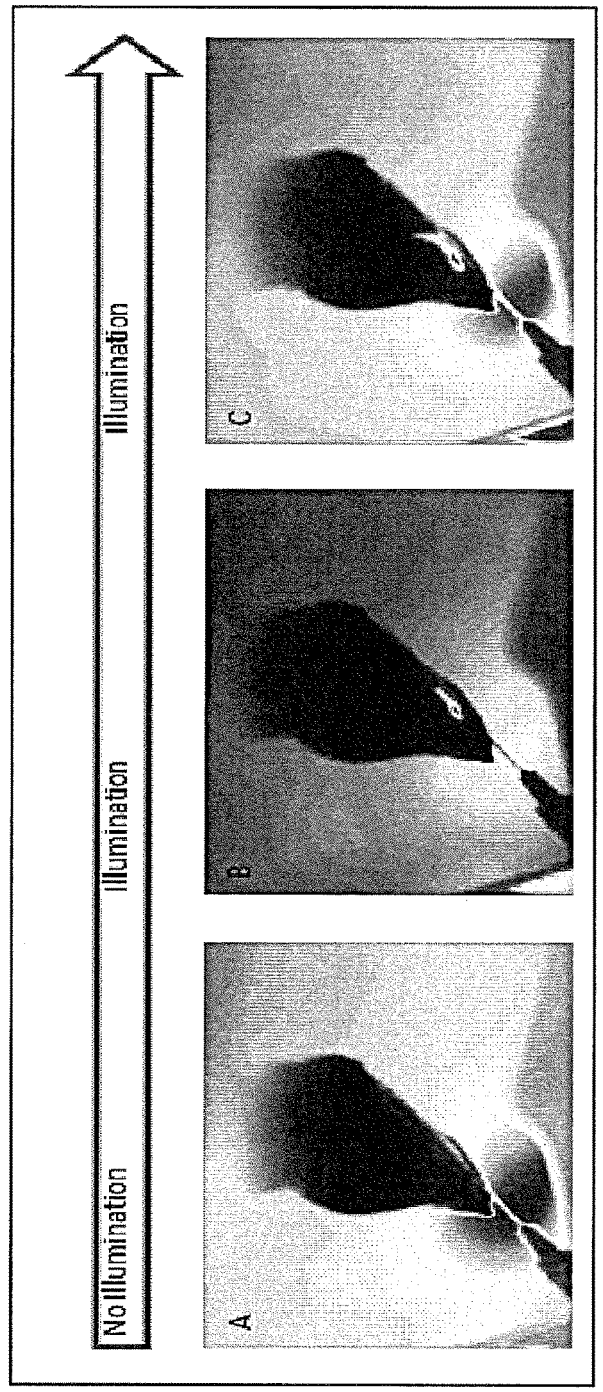
FIG. 13 illustrates images of 0.1 Hz video for 405 nm at 3840 mW/cm$^2$; this figure shows (from left to right) images of blood flow with no LED illumination, when the LED was turned on, and the moment when the LED was turned off.
Figure 14:
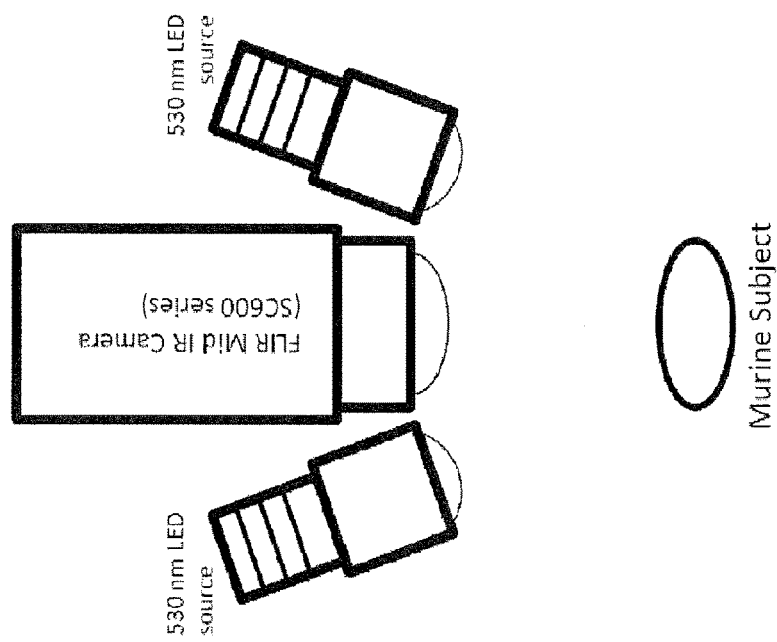
FIG. 14 is a schematic diagram illustrating the enhanced thermographic equipment of the present invention, including a FLIR SC600 series camera and two 530 nm Thorlabs LED sources; the LED sources are used to create a temperature contrast in thermal images by heating blood selectively while the mid IR camera captures these changes for analysis.

FIG. 13 shows three representative images from the video for the 0.1 Hz pulsing at 3.84 W/cm$^2$ after the Wiener filter was applied. Panel A shows an image of the heart at the beginning of the experiment. In these tests the heart was at 20° C. (not at body temperature). Panel B shows an image during LED illumination. The LED spot is clearly visible on the tissue as the bright red/yellow spot. The LED is heating the blood, vessel and some surrounding muscle tissue. Panel C shows the warmed blood moving through the blood vessel. The path of the blood vessel is evident. The temperature of the blood in the vessels was measured to be a maximum of 2.7° C. warmer than the surrounding tissue. The heating does provide a contrast and enables visualization of the vascular structure. The blood vessel seen in the thermal image does trace a blood vessel that was evident on the heart by visual inspection. However, the vessel was not evident far from the LED spot (approximately 1 cm).

We are trying to map changes in temperature to see the blood vessels. We used a time derivative to map how temperature changes with time in a region frame by frame. In our flow tests, as heated blood moves into a region the change in temperature with time will map the presence of this heated blood. A derivative image (dT/dt) was created by differencing the Nth matrix from the Nth+1 matrix and dividing by the time between each matrix (1/(video frame rate)). This method yielded interesting frames at the instances when the pulse started and stopped. We determined that the change in time was too small to pick up the changes in temperature and the algorithm was changed to the Nth matrix differenced from the Nth+9 matrix divided by the time over the 10 frames. The LED was pulsed in these experiments and this resulted in an alternating flow of warmer and cooler blood through the vessels. Heating events were when warm blood flowed through the region. Cooling events were when unheated (cooler) blood flowed through a region. The absolute value of the derivative for each frame was taken to create an image that showed both cooling and heating events. Once the derivative frames were created, they were smoothed using the Wiener filter method described previously. This smoothing was intentionally performed after the derivative image was formed to reduce the chance that small structures would be lost before being enhanced in the derivative processing. The derivative frames were then converted into a video slideshow that allowed tracking of the heated blood as it traveled through the vasculature.

This provides the processed frame at the beginning of a LED pulse. The path of the blood flow in the vessel is visible for a short distance from the LED spot by approximately 2 cm. This also shows a frame at the end of the same LED pulse. The vasculature is now visible all the way across the heart tissue for approximately 4 cm. These structures were not visible in the frames that only displayed ΔT (see FIG. 19). This further shows the frame before the next pulse is started. In this frame even more vasculature is visible across the heart for approximately 7 cm. Note, however, in this frame the location of the vasculature is visible but, the quality of the image has been degraded by heat transfer, or blooming, in the tissue. It is also important to note that since these tests were conducted near room temperature we were recording outside of the peak sensitivity of the camera. This adversely affects the focus of the images obtained. Future tests will maintain the heart and blood at an initial temperature of 37.5° C. (internal body temperature). This will allow the test to occur within the peak sensitivity of the camera as well as more accurately represent a living specimen.

The processing required to create the images took approximately 89 seconds. However, the use of a standalone imaging processing system will greatly reduce this time. Additionally, further adjustment of the program used to perform this and more efficient memory management will also speed the processing.

This method could be applied to images of the static morphology of blood vessels. The tissue testing described revealed that the heating rate for the blood was larger than the heating rate for other tissue types for the 530 nm LED. The same is likely true for the 405 nm LED, but our tissue experiments did not show this due to convective cooling of the blood sample. If an LED is flashed over a region of tissue, the areas with blood will heat more rapidly. By mapping the change in temperature with time, it will be sensitive to areas that show rapid heating.

The goal of this study was to develop a method capable of creating a temperature contrast between blood vessels and the surrounding tissue in a thermal image. Various porcine tissue types (blood, muscle, skin, and fat) were illuminated with 405 nm and 530 nm LED sources. The induced temperature change of the exposed tissue was recorded with a FLIR SC600 series mid-IR camera.

The 530 nm LED test showed that the blood experienced the largest heating and the largest heating rate when compared to the other tissues. The other tissues experienced less heating and a near constant heating rate. This demonstrates that 530 nm LED illumination is a good candidate for inducing a contrast to image blood in a thermal image.

The 405 nm LED test heated all tissues and every tissue type had a large rate of change in the heating. The blood did not heat as much as the other tissue types and experienced a lower than expected rate of heating. This was contradictory to what was expected due to blood's large absorption coefficient. The blood test was affected by convective cooling which created a reduction in the recorded temperature.

The tests which flowed blood through vessels in heart tissue showed that a contrast can be induced in the IR image by simply exposing the blood flow to the pulsed 405 nm LED source. Taking the derivative of temperature (dT/dt) and removing the noise with a 2D adaptive linear filter further enhanced contrast in the thermal images. This enhancement was successful in mapping blood vessels that were apparent by visible inspection of the tissue as well as vessels that could not be seen. In addition to location the flow of the blood was successfully mapped 7 cm from the LED spot. These tests clearly showed that the 405 nm LED can be used to create a contrast that allows mapping of blood vessels in tissue.

The medical industry has a need for high spatial resolution images of blood vessels that can be used in real-time and requires minimal training to interpret the images. Such images can aid in the surgical navigation, pre and post-surgical monitoring and breast cancer detection. MRI and CT scans have good imaging capabilities but do not provide real time imaging capabilities for applications such as surgical navigation. Ultrasound and OCT require a well-trained technician to interpret the images and the equipment required for these methods can interfere with non-contact operation. Photoacoustic imaging methods yield high-quality images but require a probe that interferes with real-time operation. Our method of thermal imaging yields images with a good spatial resolution and operates in a non-contact mode.

Our technique can be used for any surgery where knowing the location of vasculature is required. By allowing the surgeon to see the locations of the blood vessels they can avoid any unnecessary damage. It will also be useful for post-operative monitoring of procedures where the growth of new vessels and vessel repair is important to patient recovery. Breast cancer can also be detected by mapping the vessels in the breast and identifying regions of increased vessel density. By creating a low cost system the advantages of vascular imaging will be available to smaller facilities and medical facilities in developing regions.

Related to the non-invasive thermal IR detection of breast tumor development in vivo, lumpectomy coupled with radiation therapy and/or chemotherapy comprises the treatment of breast cancer for many patients. We are developing an enhanced thermal IR imaging technique that can be used in real-time to guide tissue excision during a lumpectomy. This novel enhanced thermal imaging method is a combination of IR imaging (8-10 μm) and selective heating of blood (~0.5° C.) relative to surrounding water-rich tissue using LED sources at low powers. Post-acquisition processing of these images highlights temporal changes in temperature and is sensitive to the presence of vascular structures. In this study, fluorescent, enhanced thermal and standard imaging modalities as well as physical caliper measurements were used to estimate breast cancer tumor volumes as a function of time in 19 murine subjects over a 30-day study period. Tumor volumes calculated from fluorescent imaging follow an exponential growth curve for the first 22 days of the study. Cell necrosis affected the tumor volume estimates based on the fluorescent images after Day 22. The tumor volumes estimated from enhanced thermal imaging, standard thermal imaging and caliper measurements all show exponential growth over the entire study period. A strong correlation was found between tumor volumes estimated using fluorescent imaging and the enhanced IR images and caliper measurements and enhanced IR images, indicating that enhanced thermal imaging is capable monitoring tumor growth. Further, the enhanced IR images reveal a corona of bright emission along the edges of the tumor masses. This novel IR technique could be used to estimate tumor margins in real-time during surgical procedures.

It is estimated that 231,840 women and 2,350 men will be diagnosed with breast cancer and that 40,730 will die from the disease in 2015. Lumpectomy coupled with radiation therapy and/or chemotherapy comprises the treatment of breast cancer for many patients. While mammography is an excellent imaging method for the detection of breast cancer, it cannot be used in real-time during surgical procedures to guide tissue excision. Currently x-ray, MRI, and/or ultrasound images of the breast are taken prior to surgery and used as reference during the procedure. During a lumpectomy, the tumor is removed and the tumor margins are immediately tested for the presence of cancer cells via frozen section histology. If cancer cells are found in the margins, additional tissue may be removed. This process can lead to a prolonged surgical procedures which increases the risk of complications during surgery. New methods such as photoacoustic (or optoacoustic) imaging and fluorescent imaging are being investigated to allow real time optical biopsy. However, these methods often have a limited field of view and/or are time consuming. We are developing an imaging method to help define margins that can be used in real-time during surgical procedures and is capable of imaging a large area of tissue in one acquisition.

The development of new vascular structures, angiogenesis, provides the nutrients and oxygen needed to support tumor growth and plays a key role in the generation of metastasis. By locating the vascular structures associated with breast cancer tumors, the location of tumor margins can be estimated. We are developing an enhanced thermal imaging technique to detect vascular networks associated with tumor growth. Our technique is a combination of thermal IR imaging (8-10 μm) and selective heating of blood (~0.5° C.) relative to surrounding water-rich tissue using LED sources at low powers provides. Creating enhanced contrast in thermal images is essential for the success of the technique. Blood absorbs light strongly at 530 nm, while absorption by soft tissues is lower at this wavelength. We illuminate tissue containing vessels with a light source to heat blood by <1° C. with respect to the surrounding tissue. The warm blood appears brighter in a thermal image, providing contrast between the vessels and surrounding tissue. We have successfully mapped vessels 1-2 cm below the surface of porcine muscle tissue. This method does not require injection of contrast agents or direct contact with the tissue.

In this study, we use enhanced thermal imaging to monitor the growth of breast cancer tumors in vivo using a murine model. The results of the enhanced thermal imaging are compared to fluorescent and standard thermal imaging of the same subjects as well as physical caliper measurements of tumor sizes to test the validity of using enhanced thermal imaging to monitor tumor growth. We also investigate the feasibility of using enhanced thermal imaging to estimate tumor margins.

Twenty Balb/c female mice 5-6 weeks old (20-23 grams) were purchased from Jackson laboratories and acclimatized to the Vivarium at UNC Charlotte prior to use. All experiments were approved by the Institutional Animal Care and Use Committee at UNC Charlotte and supervised by the staff veterinarian. On Day 1 of the study, animals were implanted with 5×104 4T1-RFP (558-583) breast cancer cells (Anti-Cancer, Inc) within the mammary fat pad. The injected cells used are aggressive murine mammary cancer cells syngeneic of Balb/c that mimic the later stages of breast cancer in humans. Subjects were fed per oral either saline or the angiotensin receptor antagonist Loasartan (12-15 mg/kg/day; SigmaAldrich, St Louis Mo.). Animals were weighed and tumor growth was monitored using calipers every 3-4 days. At Day 30 post tumor implantation, animals were euthanized and organs and the tumor were collected.

The physical sizes of tumors for all subjects were measured with calipers throughout the study. Every 3-4 days the length and width of the tumors was measured and recorded. This method could only be used to monitor tumor growth after the tumor was large enough to be palpable (Day 8).

All studies were performed using an IVIS Spectrum in vivo imaging system (Perkin Elmer). Sedated murine subjects were illuminated and imaged from above (epi-illumination). Four subjects were imaged simultaneously. The fluorescent response was recorded using a 2048×2048 cooled (−90° C.) CCD detector (dark current <100 electron/s/cm$^2$ and RN<5 electrons for 8 pixel binning). A 25 cm by 25 cm field of view (FOV) was used for all imaging sessions, resulting in a spatial resolution of 0.4 mm in all images. The tumor cell line used in this study was a fluorescent protein cell line with excitation and emission wavelengths of 558 nm and 583 nm, respectively. IVIS imaging was performed using a series of narrow-band filters to isolate the fluorescent signal from the cells while allowing removal of the auto fluorescence background. This spectral unmixing was performed using Living Image software. In addition to the fluorescent emission images, low light level white light images of the subjects were obtained. The fluorescent images were overlaid with the white light images to correlate the position of the tumor (seen by visual inspection late in the study) and the fluorescent emission.

Enhanced thermal imaging is a combination of IR imaging (8-10 microns) and LED illumination to induce a thermal contrast in the subjects. A FLIR SC600 series mid-IR camera (sensitive from 7.5 to 14.0 microns) with an array size of 640×480 pixels and maximum frame rate of 200 fps was used to image all subjects. A compound germanium lens system with an effective focal length of 100 mm was used with the camera, yielding a spatial resolution of 0.26 mm. Two LED sources with a peak wavelength of 530 nm (Thorlabs M530L2) were used to illuminate the subjects during imaging. The LED sources have a maximum power output of 1000 mW and spectral width of 16 nm. The output from each LED was collimated using an aspheric optic and the LED sources were controlled using a high power LED driver (Thorlabs DC2100). The illumination area had a 4 cm diameter yielding an average power density of 283 mW/cm$^2$.

Enhanced thermal images were taken on Day 1 both before and immediately after the injection of breast cancer cells and then periodically throughout the study. The murine subjects were placed under anesthesia so that they remained stationary during all imaging sessions. During each imaging session, 4 sets of enhanced thermal images were acquired for each subject. For each image set, the tumor and surrounding tissue were illuminated with the LED sources for 10 seconds. The thermal camera recorded the temperature of the tumor and surrounding area before, during and after LED illumination. The imaging sets were separated by 15 seconds to insure cooling of the tissue. LED illumination heated the blood/vascular networks around the tumor regions by approximately 0.5° C. This selective heating provided contrast in the thermal images but was well below the tissue damage threshold. During imaging a stainless steel washer was place on the subject's abdomen just forward of the urethra to aid with image alignment in post-acquisition processing.

In addition to enhanced thermal images, standard thermal images were also obtained to monitor tumor development. No LED illumination was used when these images were taken (i.e. there was no selective heating of blood or blood vessels). The thermal camera recorded the natural temperature gradients across the tumor and surrounding tissue. These thermal images were obtained using the same camera (FLIR SC600) and experimental setup as was used for enhanced thermal imaging. All images used for the purpose of standard thermographic analysis were captured in the first 5 seconds of each imaging session. The first 5 frames from this period were averaged into a single thermographic image and a light noise reduction routine applied to them in Matlab.

To monitor tumor growth, the volume of the tumor was calculated following the method described by Feldman et al. (see Equation 11). The tumor volume was estimated from the area and/or the two-dimensional major and minor axes of the tumor as measured in the IVIS and enhanced thermal images.

Equation 11: Feldman Volume $$V = \frac{\pi}{6} f (\text{Length} * \text{Width})^{\frac{3}{2}}$$

$$f = 1.58 \pm 0.01 \text{ (Female Murine Subjects)}$$

An average tumor volume of all subjects (n=19) was calculated on each day that imaging was performed. Errors were estimated based on the standard deviation from the mean.

Figure 15:
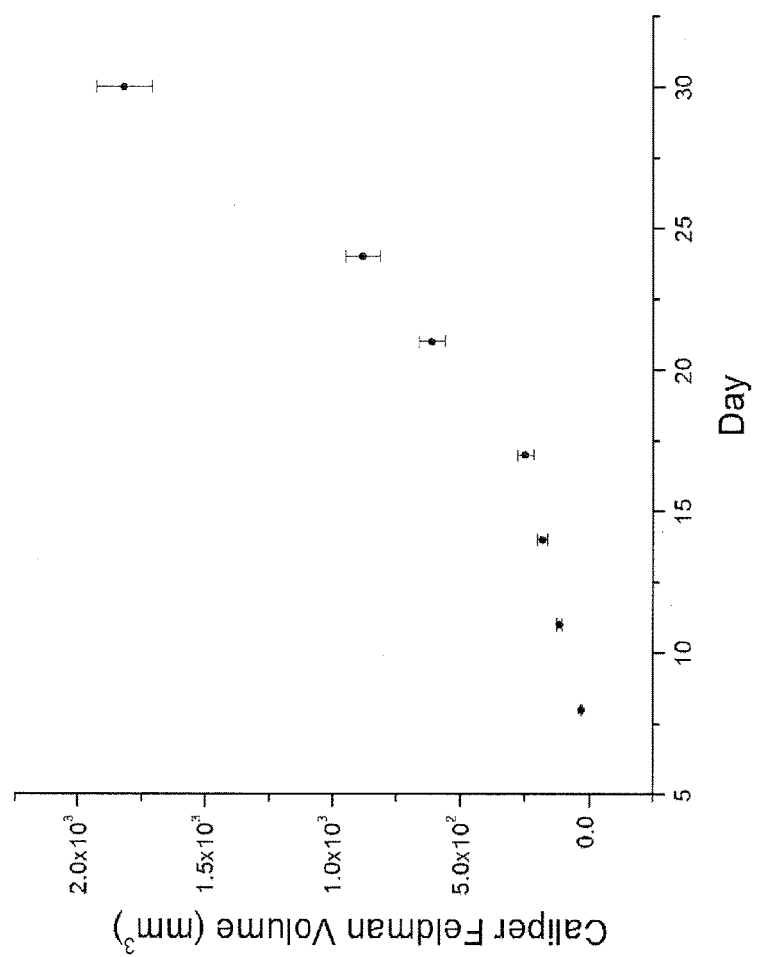
FIG. 15 is a plot illustrating average tumor volume (n=19) as a function of time based on caliper measurements; approximately exponential tumor growth is evident throughout the study; measurement before Day 8 was not possible because the tumors were not palpable; errors are standard deviation from the mean.

Using calipers we were able to physically measure the length and width of tumors from Day 8 forward until the end of the study. Physical measurement was not possible prior to day 8 because the tumors were too small to be palpable. Tumor volumes, based on the measured lengths and widths, were calculated using the Feldman method. Average tumor volume as a function of time is shown in FIG. 15. The caliper measurements show the expected exponential tumor growth.

A typical IVIS image was obtained from Day 14 in the study. The tumor mass was clearly visible in the image. The number of pixel exhibiting fluorescent emission was determined using MATLAB for each subject. This pixel area was then used as the elliptical area (length×width term) in the Feldman formula for tumor volume.

Figure 16:
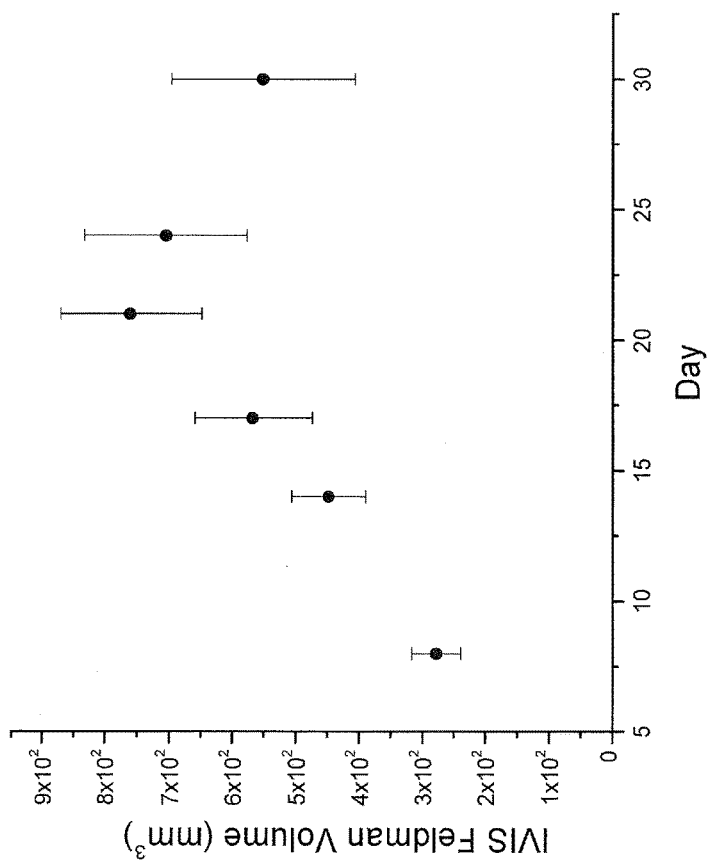
FIG. 16 is a plot illustrating average tumor volume (n=19) as a function of time based on IVIS images; approximately exponential tumor growth is evident during the first 22 days of the study; after Day 22, volumes decrease due to tumor cell necrosis; errors are standard deviation from the mean.

Average tumor volume as a function of time is shown in FIG. 16. As expected, IVIS imaging detected the presence of cancer cells on Day 1 of the study (day that cells were implanted) as this imaging method is sensitive to the fluorescence of the injected cancer cells. Tumor growth is approximately exponential from Day 1 to Day 22 of the study. After Day 22 the tumor volume, as calculated from the IVIS images, begins to decline. The fluorescent signal detected by the IVIS imaging system is proportional to the overall number of living cancer cells present in the tumor. IVIS does not detect cells that have died. After Day 22 cell death (necrosis) begins to have a significant effect on the IVIS results. White light images of the tumor clearly show necrosis on the later days of the study (See FIG. 4). In addition, as the tumor mass increases in size, fluorescent excitation of the cells deep in the tumor mass becomes difficult or impossible as the incoming excitation signal cannot propagate deeply into the tissue.

Figure 17:
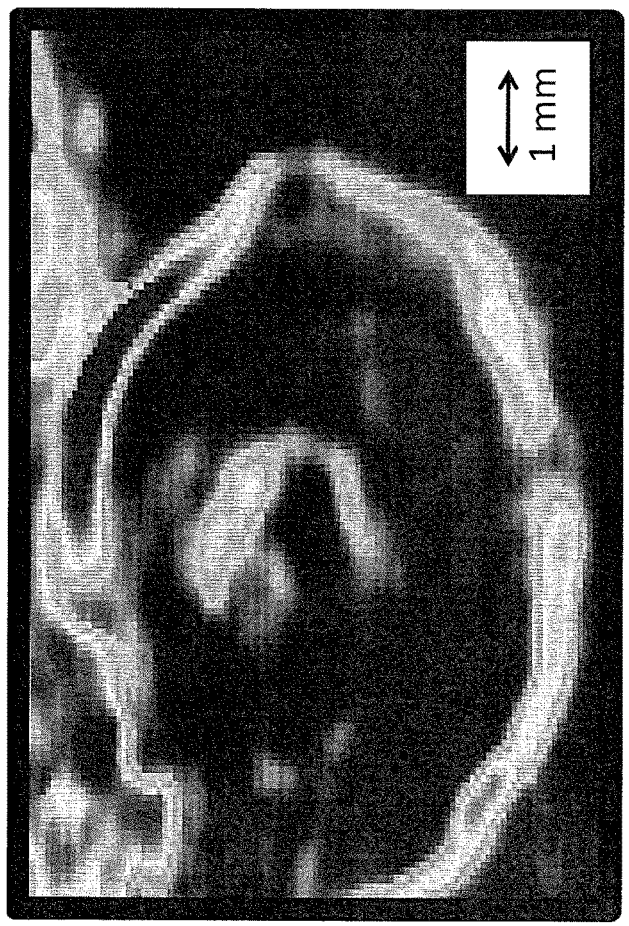
FIG. 17 illustrates the temporal derivative of the enhanced thermal images of a tumor mass in a typical subject on Day 28 of the study; notice the yellow/green ring evident in the image; his ring delineates the edges of the tumor mass; the temperature difference between the blood rich corona and the surrounding tissue after LED illumination is approximately 0.4° C.

Enhanced thermal images were processed after acquisition using a temporal derivative method that is sensitive to changes in temperature with time. The blood and vessels heat more than the surrounding tissue upon LED illumination as energy from the LED is strongly absorbed by blood in these regions. This temporal derivative method highlights vascular structures by revealing regions of rapid temperature change during LED illumination. Tumors were evident in the enhanced thermal images on Day 7 of the study (the first time subjects were imaged after the initial injection of tumor cells) and tumor growth was monitored for the remainder of the study. FIG. 17 shows the temporal derivative of the enhanced thermal images for a typical subject on Day 28 of the study. The green/yellow ring highlights the edges of the tumor mass. This ring is associated with a large temperature change upon LED illumination. LED illumination produce a temperature difference of approximately 0.4° C. between the blood rich corona and the surrounding tissue. The major and minor axes of the tumor were estimated by interactively selecting the length and width from each image using MATLAB. The circular object seen in the lower left corner is a stainless steel marker used for post processing image alignment.

Figure 18:
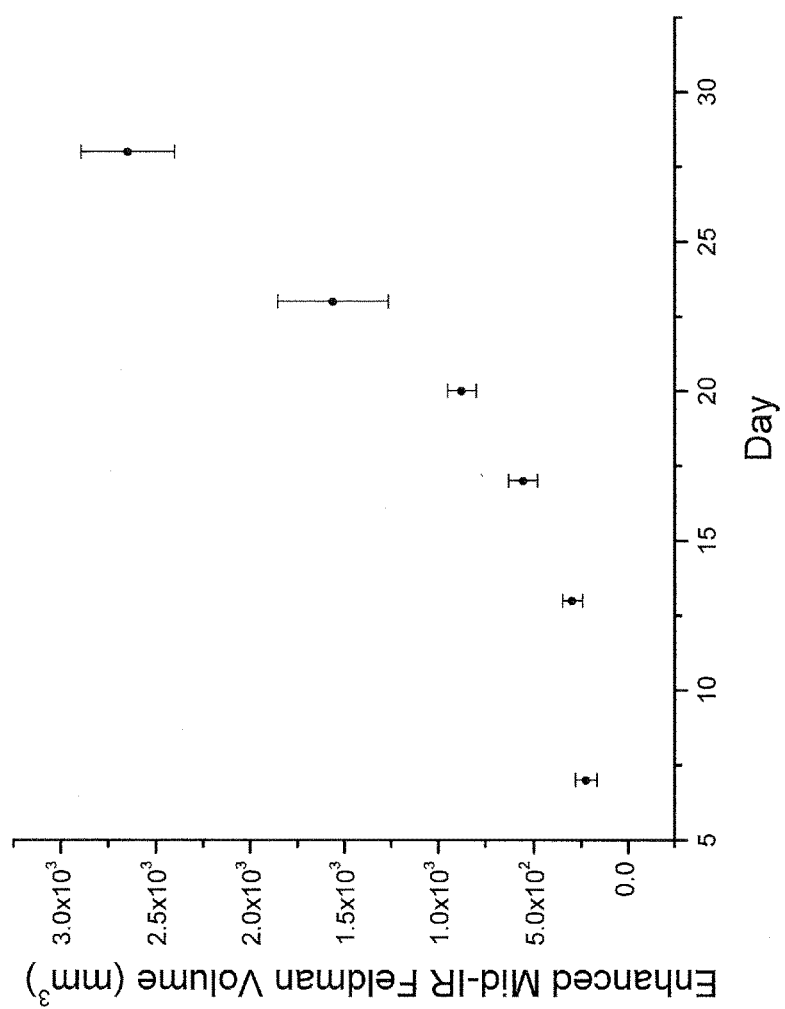
FIG. 18 illustrates average tumor volume (n=19) as a function of time based on the enhanced thermal images; approximately exponential tumor growth is evident during all days of the study; errors are standard deviation from the mean.

An average tumor volume (n=19) was calculated on each day. Average tumor volume as a function of time is shown in FIG. 18. The tumor volume increases exponentially with time, similar to the results seen for the caliper measurements and for the IVIS imaging before Day 22. Unlike IVIS imaging, the tumor volume estimates from the enhanced thermal images are not sensitive to cell necrosis and the exponential growth trend continues until the end of the study.

Standard thermal imaging was also used to monitor tumor growth after Day 7 of the study (images were not taken before Day 8). No LED illumination was used when these images were taken (i.e. there was no selective heating of blood or blood vessels). The thermal imaging is sensitive to natural temperature differences between the tumor mass and the surrounding tissue. A 2D adaptive filter was applied to each of the images using MATLAB. The tumor was clearly visible, but the tumor edges are not as clearly defined as in the enhanced thermal images. The tumor mass is about 1° C. cooler that the surrounding healthy tissue, likely due to necrosis and poor profusion of the tumor at this late stage of the study. The x and y axes of the tumor were estimated using MATLAB based on the images. An average tumor volume (n=19) was calculated on each of these days. The tumor volume increases exponentially with time, similar to the results seen for the caliper measurements and both IVIS and enhanced thermal imaging.

Caliper measurements physically determine the size a tumor and accurately monitor tumor growth. We have compared the tumor growth measured using IVIS, enhanced thermal imaging, and standard thermal imaging to access the effectiveness of each of these techniques at monitoring tumor growth. In all cases the measurements exhibit a strong linear correlation, meaning that the imaging techniques are all effectively monitoring tumor growth.

Figure 19:
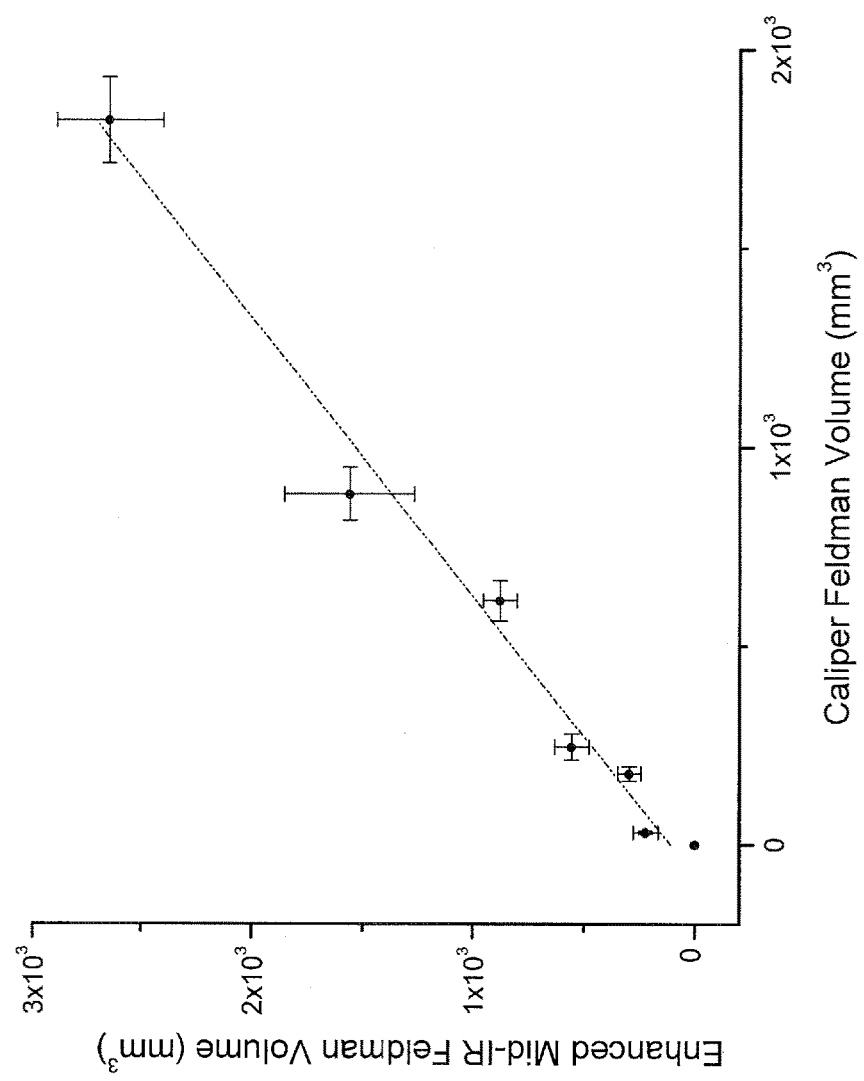
FIG. 19 illustrates enhanced mid-IR versus physical caliper correlation correlating our enhanced thermographic technique to physical caliper measurement, which yields a linear relationship (Adjusted R2=0.98); from this we can see that our method measures approximately 43 percent (Slope=1.43) more tumor volume; this is due to the fact that our method focuses on the blood rich corona surrounding the tumor and not the tumor mass directly.

FIG. 19 shows the correlation plot for tumor volumes measured with calipers compared to the volumes estimated by enhanced thermal imaging. Tumors were not detected with caliper measurements or enhanced thermal imaging until Day 7 of the study, so only Days 7-30 are included in the correlation plot. The tumor volumes measured by calipers and the standard thermal images are strongly correlated (Adjusted $R^2$=0.98). The linear fit to the correlation (slope=1.43) indicates that the enhanced thermal imaging measured volumes that were approximately 43% larger than those estimated based on the caliper measurements throughout the study period.

Figure 20:
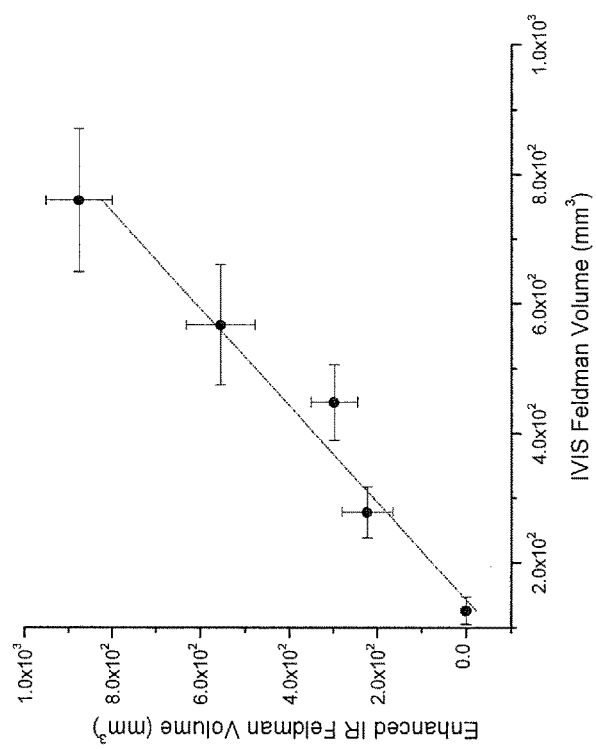
FIG. 20 illustrates correlation of volumes calculated based on the IVIS images and those calculated from the enhanced thermal images; the volume estimates are well correlated (Adjusted R2=0.949) with a slope of 1.34.

Enhanced IR vs. IVIS: The IVIS fluorescent imaging is sensitive to the presence of cancer cells. As the number of cancer cells increases, the fluorescent signal increases and the estimated tumor volume increases. IVIS imaging directly tracks the growth of the tumors over time. A correlation plot for the tumor volumes calculated using enhanced thermal imaging and IVIS imaging is shown in FIG. 20. Only Days 7-21 are included in the correlation plot. On the first day of the study tumors were not detected with enhanced thermal imaging and after Day 21, cell necrosis affected the IVIS estimates. The tumor volumes measured by the IVIS and enhanced thermal images are strongly correlated (Adjusted $R^2$=0.949). This indicates that the enhanced thermal imaging is also measuring tumor growth. The linear fit to the correlation (slope=1.34) indicates that the enhanced thermal imaging measured volumes that were approximately 34% larger than those estimated based on IVIS imaging throughout the study period. The larger volume is likely due to fact that the enhanced thermal imaging is sensitive to vascular structures immediately outside the tumor mass, while the IVIS images trace cells inside the tumor mass.

Figure 21:
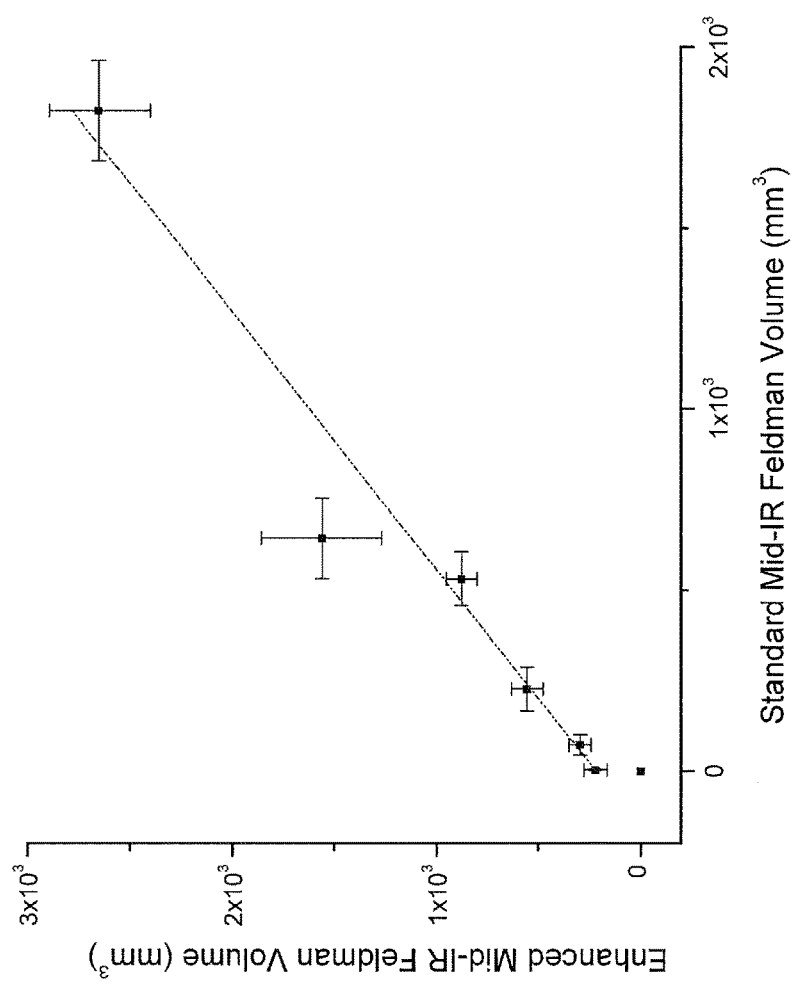
FIG. 21 illustrates enhanced mid-IR versus standard mid-IR correlation correlating our enhanced thermographic technique to standard thermographic methods, which yields a linear relationship (Adjusted R2=0.94); from this we can see that our method measures approximately 40 percent (Slope=1.40) more tumor volume; this is due to the fact that our method focuses on the blood rich corona surrounding the tumor and not the tumor mass directly.

FIG. 21 shows the correlation plot for tumor volumes measured with enhanced thermal imaging compared to the volumes estimated by standard thermal imaging. Tumors were not detected with either imaging method until Day 7 of the study, so only Days 7-30 are included in the correlation plot. The tumor volumes measured by the enhanced thermal images and the standard thermal images are strongly correlated (Adjusted $R^2$=0.94). The linear fit to the correlation (slope=1.40) indicates that the enhanced thermal imaging measured volumes that were approximately 40% larger than those estimated based on standard thermal imaging throughout the study period.

The results of this study indicate that the enhanced thermal imaging technique described here is a viable means for detecting tumor growth. Further, enhanced thermal imaging is capable of highlighting a blood rich corona around tumors. This corona is likely associated with the margin of the tumor mass. Enhanced thermal imaging could become a viable indicator of tumor margins that could be used in real-time during surgical procedures. While estimates of tumor volume based on fluorescent imaging techniques are negatively affected by cell necrosis, estimates of tumor volume based on the enhanced thermal images are not affected by the presence of necrotic tissue within the tumor mass.

Although the present invention is illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the present invention, are contemplated thereby, and are intended to be covered by the following non-limiting claims.

What is claimed is:

1. A method for imaging a vascular anatomical structure, comprising:
   selectively heating the vascular anatomical structure relative to an adjacent anatomical structure by exposing the vascular anatomical structure to radiation using an optical source;
   imaging the heated vascular anatomical structure using a thermal imaging camera to obtain an image;
   processing the image using one or more of a spatial derivative analysis to find regions with steep spatial temperature gradients and a temporal derivative analysis to find regions with rapid heating; and
   displaying the image on a display.

2. The method of claim 1, further comprising using the regions found to determine the margins of a solid mass tumor.

3. The method of claim 2, further comprising superimposing the margins of the solid mass tumor on another image of the solid mass tumor to provide a map for excising the solid mass tumor.

4. The method of claim 1, wherein the vascular anatomical structure is heated by about 0.5° C. relative to the adjacent anatomical structure.

5. The method of claim 1, wherein the optical source comprises one of a light emitting diode and a laser.

6. The method of claim 5, wherein the one of the light emitting diode and the laser is operated in one of a pulsed mode and a continuous mode.

7. The method of claim 1, wherein the radiation has a wavelength of one of about 420 nm and about 530 nm.

8. The method of claim 1, wherein the thermal imaging camera is a mid-infrared thermal imaging camera.

9. A system for imaging a vascular anatomical structure, comprising:
   an optical source for selectively heating the vascular anatomical structure relative to an adjacent anatomical structure by exposing the vascular anatomical structure to radiation;
   a thermal imaging camera for imaging the heated vascular anatomical structure to obtain an image;
   a processor executing an algorithm for processing the image using one or more of a spatial derivative analysis to find regions with steep spatial temperature gradients and a temporal derivative analysis to find regions with rapid heating; and
   a display for displaying the image.

10. The system of claim 9, further comprising means for using the regions found to determine the margins of a solid mass tumor.

11. The system of claim 10, further comprising means for superimposing the margins of the solid mass tumor on another image of the solid mass tumor to provide a map for excising the solid mass tumor.

12. The system of claim 9, wherein the vascular anatomical structure is heated by about 0.5° C. relative to the adjacent anatomical structure.

13. The system of claim 9, wherein the optical source comprises one of a light emitting diode and a laser.

14. The system of claim 13, wherein the one of the light emitting diode and the laser is operated in one of a pulsed mode and a continuous mode.

15. The system of claim 9, wherein the radiation has a wavelength of one of about 420 nm and about 530 nm.

16. The system of claim 9, wherein the thermal imaging camera is a mid-infrared thermal imaging camera.

17. A method for imaging a vascular anatomical structure, comprising:
   selectively heating the vascular anatomical structure relative to an adjacent anatomical structure by exposing the vascular anatomical structure to radiation using an optical source;
   imaging the heated vascular anatomical structure using a thermal imaging camera;
   processing the image using a spatial derivative analysis to find regions with steep spatial temperature gradients and a temporal derivative analysis to find regions with rapid heating;
   using the regions found to determine the margins of the vascular anatomical structure; and
   displaying the processed image and the margins on a display.

* * * * *